US007853069B2

(12) United States Patent
Katayama et al.

(10) Patent No.: US 7,853,069 B2
(45) Date of Patent: Dec. 14, 2010

(54) STEREOSCOPIC IMAGE REGENERATING APPARATUS, STEREOSCOPIC IMAGE REGENERATING METHOD, AND STEREOSCOPIC IMAGE REGENERATING PROGRAM

(75) Inventors: Eisaku Katayama, Tokyo (JP); Norio Baba, Tokyo (JP); Yoshitaka Kimori, Tokyo (JP)

(73) Assignees: The University of Tokyo, Tokyo (JP); TOUDAI TLO, Ltd., Tokyo (JP)

( * ) Notice: Subject to any disclaimer, the term of this patent is extended or adjusted under 35 U.S.C. 154(b) by 833 days.

(21) Appl. No.: 11/810,632

(22) Filed: Jun. 6, 2007

(65) Prior Publication Data
US 2007/0253612 A1 Nov. 1, 2007

Related U.S. Application Data

(63) Continuation of application No. PCT/JP2005/022471, filed on Dec. 7, 2005.

(30) Foreign Application Priority Data
Dec. 7, 2004 (JP) ............................. 2004-354563

(51) Int. Cl.
*G06K 9/00* (2006.01)
(52) U.S. Cl. ..................... 382/154; 382/285; 345/419; 356/12; 348/42
(58) Field of Classification Search .............. 382/154, 382/285; 345/419–427; 356/12–14; 348/42–60; 359/462–477; 352/57–65; 33/20.4; 353/7–9; 378/41–42; 396/324–331
See application file for complete search history.

(56) References Cited

U.S. PATENT DOCUMENTS
4,149,247 A * 4/1979 Pavkovich et al. ............ 378/14
(Continued)

FOREIGN PATENT DOCUMENTS
JP 8-292164 11/1996
(Continued)

OTHER PUBLICATIONS
International Search Report issued in International Application No. PCT/JP2005/022471 mailed on Feb. 7, 2006 and English translation thereof, 8 pages.
(Continued)

*Primary Examiner*—Aaron W Carter
(74) *Attorney, Agent, or Firm*—Osha Liang LLP

(57) ABSTRACT

There is provided a three-dimensional image reconstructing apparatus for reconstructing a three-dimensional image of an object. The three-dimensional image reconstructing apparatus includes an image-capturing section that captures a plurality of transmission-type images each of which is represented by densities of different levels, a characteristic region selecting section that selects a plurality of characteristic regions in each of the transmission-type images, a characteristic region distribution calculating section that calculates a spatial distribution of the characteristic regions based on respective positions of the characteristic regions, in each of the transmission-type images, and a three-dimensional image reconstructing section that, when reconstructing the three-dimensional image which shows the three-dimensional structure of the object and in which the densities of different levels are allocated to the whole object by integrating the transmission-type images, allocates the densities of different levels of the transmission-type images to respective positions, in the three-dimensional image, of the characteristic regions based on the spatial distribution of the characteristic regions, so as to reconstruct the three-dimensional image in which a three-dimensional structure in each of the characteristic regions is shown.

16 Claims, 19 Drawing Sheets

U.S. PATENT DOCUMENTS

| | | | | |
|---|---|---|---|---|
| 4,149,248 | A | * | 4/1979 | Pavkovich .................. 378/14 |
| 4,149,249 | A | * | 4/1979 | Pavkovich .................. 378/14 |
| 4,365,339 | A | * | 12/1982 | Pavkovich et al. ............ 378/15 |
| 5,278,408 | A | * | 1/1994 | Kakibayashi et al. ....... 250/311 |
| 5,414,261 | A | * | 5/1995 | Ellisman et al. ............. 250/311 |
| 5,475,218 | A | * | 12/1995 | Kakibayashi et al. ....... 250/311 |
| 5,552,602 | A | * | 9/1996 | Kakibayashi et al. ....... 250/311 |
| 5,866,905 | A | * | 2/1999 | Kakibayashi et al. ....... 250/311 |
| 6,051,834 | A | * | 4/2000 | Kakibayashi et al. ....... 250/311 |
| 6,418,243 | B1 | * | 7/2002 | Skoglund et al. ............ 382/274 |
| 6,531,697 | B1 | * | 3/2003 | Nakamura et al. .......... 250/311 |
| 6,828,555 | B2 | * | 12/2004 | Katayama et al. ........... 250/311 |
| 7,379,582 | B2 | * | 5/2008 | Katayama et al. ........... 382/154 |
| 7,538,329 | B2 | * | 5/2009 | Chen et al. ............. 250/370.11 |
| 7,639,865 | B2 | * | 12/2009 | Katayama et al. ........... 382/154 |
| 2004/0041806 | A1 | * | 3/2004 | Katayama et al. ........... 345/419 |
| 2004/0069946 | A1 | * | 4/2004 | Katayama et al. ........... 250/311 |
| 2007/0063154 | A1 | * | 3/2007 | Chen et al. ............... 250/483.1 |
| 2007/0253612 | A1 | * | 11/2007 | Katayama et al. ........... 382/128 |

FOREIGN PATENT DOCUMENTS

| | | |
|---|---|---|
| JP | 2002-109516 | 4/2002 |
| JP | 2003-583 | 1/2003 |
| JP | 2004-132944 | 4/2004 |
| WO | WO-02/48961 | 6/2002 |

OTHER PUBLICATIONS

English abstract of WO/2002/048961 published Jun. 20, 2002, 2 pages.

A. Argyros et al., "Electron Tomography and Computer Visualisation of a Three-Dimensional 'Photonic' Crystal in a Butterfly Wing-Scale", Micron, vol. 33, Issue 5, 2002, pp. 483 to 487.

Ulrike Ziese et al., "Perspective—Electron Tomography: A Tool for 3D Structural Probing of Heterogeneous Catalysts at The Nanometer Scale", Applied Catalysis A: General, vol. 260, Issue 1, Mar. 25, 2004, pp. 71 to 74.

* cited by examiner

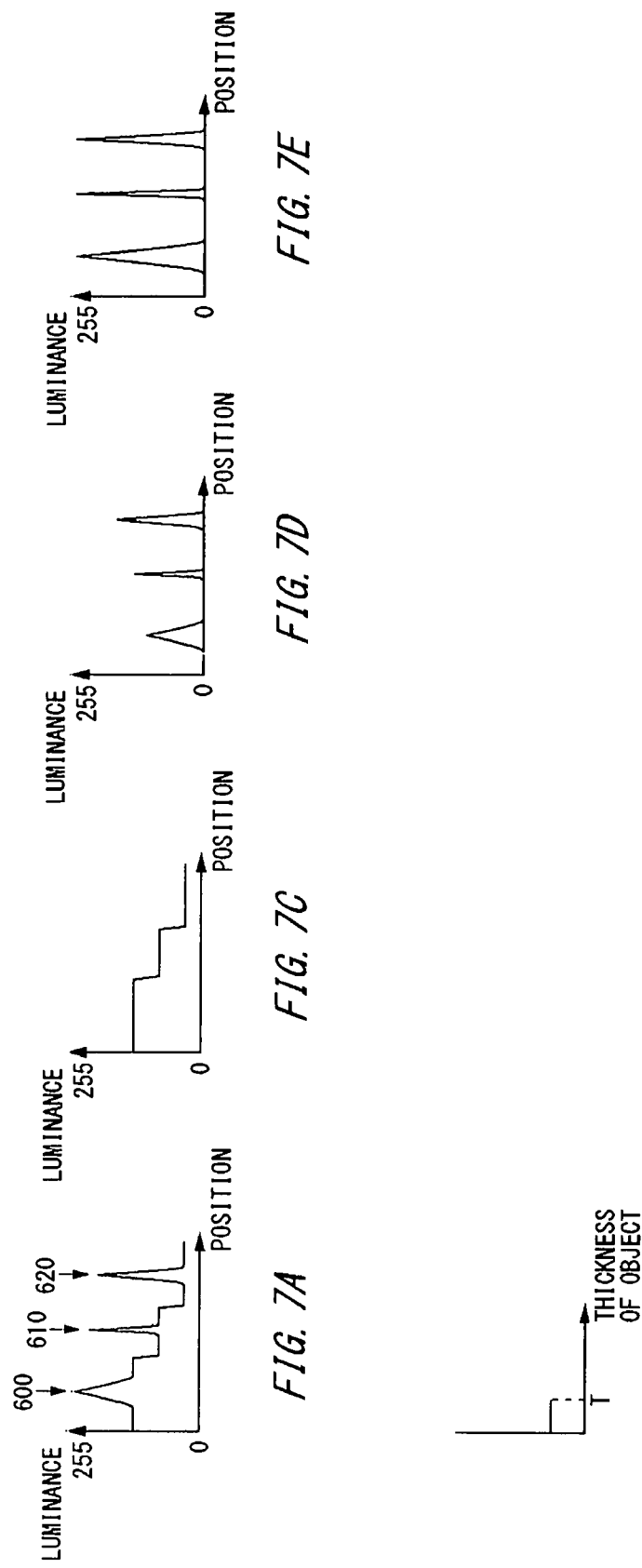

STEREOSCOPIC IMAGE REGENERATING APPARATUS, STEREOSCOPIC IMAGE REGENERATING METHOD, AND STEREOSCOPIC IMAGE REGENERATING PROGRAM

CROSS REFERENCE TO RELATED APPLICATION

This is a continuation application of PCT/JP2005/022471 filed on Dec. 7, 2005 which claims priority from a Japanese Patent Application No. 2004-354563 filed on Dec. 7, 2004, the contents of which are incorporated herein by reference.

BACKGROUND

1. Technical Field

The present invention relates to a three-dimensional image reconstructing apparatus, a three-dimensional image reconstructing method, and a three-dimensional image reconstructing program. More particularly, the present invention relates to a three-dimensional image reconstructing apparatus, a three-dimensional image reconstructing method, and a three-dimensional image reconstructing program for reconstructing a three-dimensional image which shows the three-dimensional structure of an object based on images of the object obtained by image-capturing the object.

2. Related Art

A three-dimensional image reconstructing apparatus has been conventionally proposed which reconstructs a three-dimensional image which shows the three-dimensional structure of an object in the following manner. A plurality of transmission-type images are obtained by image-capturing the object from a plurality of different angles by way of a transmission electron microscope. The planar transmission-type images are extended in the direction in which the respective images are captured and then integrated to each other. By doing so, the above-mentioned three-dimensional image is reconstructed by integrating the densities of different levels. In addition, another three-dimensional image reconstructing apparatus has been proposed which reconstructs a more accurate three-dimensional image of an object, not only by extending a plurality of planar transmission-type images in the respective image-capturing directions and integrating the resulting images so that the densities of different levels are integrated but also by using morphological information indicating the outline of the object which is calculated based on the captured transmission-type images, as disclosed in International Publication No. WO2002/048961, for example However, the region shown by extending the transmission-type images in the image-capturing directions and integrating the resulting images so as to integrate the densities of different levels includes a region called "a phantom" in which the object is actually not present, due to a special way of how a specimen is supported in the electron microscope. Therefore, the three-dimensional image which is reconstructed only by integrating the densities of different levels in the above-described manner has a problem of low accuracy. Furthermore, the three-dimensional image which is reconstructed based further on the morphological information indicating the outline of the object does not contain information indicating the internal structure of the object. For this reason, the three-dimensional image reconstructing apparatus disclosed in the publication No. WO2002/048961 can not be utilized to enable a user to know the internal structure of the object.

In view of the above, an advantage of some embodiments of the present invention is to provide a three-dimensional image reconstructing apparatus, a three-dimensional image reconstructing method, and a three-dimensional image reconstructing program which can solve the above-described problem. This advantage is achieved by combining the features recited in the independent claims. The dependent claims define further effective specific example of the present invention.

SUMMARY

To solve the above-described problem, a first embodiment of the present invention provides a three-dimensional image reconstructing apparatus for reconstructing a three-dimensional image showing a three-dimensional structure of an object based on an image of the object which is obtained by image-capturing the object. The three-dimensional image reconstructing apparatus includes an image-capturing section that captures a plurality of transmission-type images by transmitting an electron beam through the object from a plurality of different angles, where the individual captured transmission-type images are represented by densities of different levels and include the object, a characteristic region selecting section that selects a plurality of characteristic regions included in the object in each of the transmission-type images, a characteristic region distribution calculating section that calculates respective spatial positions of the characteristic regions in the whole object based on respective positions of the characteristic regions, in each of the transmission-type images, which are selected in each of the transmission-type images, so as to calculate a spatial distribution of the characteristic regions in the whole object, and a three-dimensional image reconstructing section that, when reconstructing the three-dimensional image which shows the three-dimensional structure of the object and in which the densities of different levels are allocated to the whole object by integrating the transmission-type images, allocates the densities of different levels of the transmission-type images to respective positions, in the three-dimensional image, of the characteristic regions based on the spatial distribution of the characteristic regions in the whole object, so as to reconstruct the three-dimensional image in which a three-dimensional structure in each of the characteristic regions is shown.

The three-dimensional image reconstructing apparatus may further include a three-dimensional structure information input section that receives information indicating an approximate three-dimensional structure of the object, and an enhancement processing section that performs image processing to enhance the object in each of the transmission-type images based on the received information indicating the approximate three-dimensional structure. Here, the characteristic region selecting section may select the characteristic regions included in the object which is enhanced by the enhancement processing section, in each of the transmission-type images. The characteristic region distribution calculating section may calculate the respective spatial positions of the characteristic regions in the whole object, based on a position, in each of the transmission-type images, of an outline of the object which is included in each of the characteristic regions. The image-capturing section may capture the transmission-type images each including the object an inside of which is stained, or the inside of which is not stained but which has a three-dimensional structure based on a density distribution. The three-dimensional image reconstructing apparatus may further include a matching operation calculating section that calculates an image processing operation to determine the densities of a three-dimensional image, which is reconstructed by the three-dimensional image reconstructing section, of any of the characteristic regions which has a known three-dimensional structure, so that the densities of the three-dimensional image of the characteristic region which has the known three-dimensional structure match the known three-dimensional structure, and a matching operation section that performs the image processing operation calculated by the matching operation calculating section on densities of a three-dimensional image, which is reconstructed by the three-dimensional image reconstructing section, of any of the characteristic regions which has an unknown three-dimensional structure.

The three-dimensional image reconstructing section may include a thickness calculating section that calculates a thickness of the object in a direction in which the electron beam is transmitted through the object, based on the spatial distribution of the characteristic regions which is calculated by the characteristic region distribution calculating section, and a infinitesimal region allocating section that divides, into a plurality of infinitesimal regions, a region within the thickness of the object which is calculated by the thickness calculating section, and allocates densities of different levels to the infinitesimal regions in compliance with the densities of different levels of the transmission-type images captured by the image-capturing section. The infinitesimal region allocating section may (i) divide each of the transmission-type images into a plurality of infinitesimal regions in correspondence with the infinitesimal regions making up the region within the thickness of the object, (ii) allocate integral values determined in proportion to the densities of different levels respectively to the infinitesimal regions included in each of the transmission-type images, and (iii) allocate binary values each indicating a density to the infinitesimal regions making up the region within the thickness in such a manner that a total value of binary values each indicating a density which are allocated to some of the infinitesimal regions making up the region within the thickness which correspond to an angle from which each of the transmission-type images is captured becomes equal to an integral value indicating a density which is allocated to a corresponding one of the infinitesimal regions included in each of the transmission-type images. The three-dimensional image reconstructing apparatus may further include a three-dimensional structure information input section that receives information indicating known facts about the three-dimensional structure of the object. Here, the infinitesimal region allocating section may allocate the densities of different levels to the infinitesimal regions in compliance with the information indicating the known facts which is received by the three-dimensional structure information input section.

To solve the above-mentioned problem, a second embodiment of the present invention provides a three-dimensional image reconstructing apparatus for reconstructing a three-dimensional image showing a three-dimensional structure of an object based on an image of the object which is obtained by image-capturing the object. The three-dimensional image reconstructing apparatus includes an image-capturing section that captures a plurality of transmission-type images by transmitting an electron beam through the object from a plurality of different angles, where the transmission-type images each are represented by densities of different levels and include the object, and a infinitesimal region allocating section that divides, into a plurality of infinitesimal regions, a region within a predetermined thickness relating to the object, and reconstructs the three-dimensional image of the object by allocating a density of a certain level to each of the infinitesimal regions in compliance with the densities of different levels of the transmission-type images captured by the image-capturing section. The infinitesimal region allocating section may (i) divide each of the transmission-type images into a plurality of infinitesimal regions in correspondence with the infinitesimal regions making up the region within the thickness of the object, (ii) allocate integral values determined in proportion to the densities of different levels respectively to the infinitesimal regions included in each of the transmission-type images, and (iii) allocate binary values each indicating a density to the infinitesimal regions making up the region within the thickness in Such a manner that a total value of binary values each indicating a density which are allocated to some of the infinitesimal regions making up the region within the thickness which correspond to an angle from which each of the transmission-type images is captured becomes equal to an integral value indicating a density which is allocated to a corresponding one of the infinitesimal regions included in each of the transmission-type images. The three-dimensional image reconstructing apparatus may further include a three-dimensional structure information input section that receives information indicating known facts about the three-dimensional structure of the object. Here, the infinitesimal region allocating section may allocate the densities of different levels to the infinitesimal regions in compliance with the information indicating the known facts which is received by the three-dimensional structure information input section.

A third embodiment of the present invention provides a three-dimensional image reconstructing method for reconstructing a three-dimensional image showing a three-dimensional structure of an object based on an image of the object which is obtained by image-capturing the object. The three-dimensional image reconstructing method includes capturing a plurality of transmission-type images by transmitting an electron beam through the object from a plurality of different angles, where the captured transmission-type images each are represented by densities of different levels and include the object, selecting a plurality of characteristic regions included in the object in each of the transmission-type images, calculating respective spatial positions of the characteristic regions in the whole object based on respective positions of the characteristic regions, in each of the transmission-type images, which are selected in each of the transmission-type images, so as to calculate a spatial distribution of the characteristic regions in the whole object, and allocating the densities of different levels of the transmission-type images to respective positions, in the three-dimensional image, of the characteristic regions based on the spatial distribution of the characteristic regions in the whole object, so as to reconstruct the three-dimensional image in which a three-dimensional structure in each of the characteristic regions is shown, when the three-dimensional image which shows the three-dimensional structure of the object and in which the densities of different levels are allocated to the whole object is reconstructed by integrating the transmission-type images.

A fourth embodiment of the present invention provides a three-dimensional image reconstructing method for reconstructing a three-dimensional image showing a three-dimensional structure of an object based on an image of the object which is obtained by image-capturing the object. The three-dimensional image reconstructing method includes capturing a plurality of transmission-type images by transmitting an electron beam through the object from a plurality of different angles, where the transmission-type images each are represented by densities of different levels and include the object, and dividing, into a plurality of infinitesimal regions, a region within a predetermined thickness relating to the object, and reconstructing the three-dimensional image of the object by allocating a density of a certain level to each of the infinitesimal regions in compliance with the densities of different levels of the transmission-type images captured in the image-capturing.

A fifth embodiment of the present invention provides a computer readable medium storing thereon a three-dimensional image reconstructing program which causes a computer to function as a three-dimensional image reconstructing apparatus for reconstructing a three-dimensional image showing a three-dimensional structure of an object based on an image of the object which is obtained by image-capturing the object. The program causes the computer to function as an image-capturing section that captures a plurality of transmission-type images by transmitting an electron beam through the object from a plurality of different angles, where the captured transmission-type images each are represented by densities of different levels and include the object, a characteristic region selecting section that selects a plurality of characteristic regions included in the object in each of the transmission-type images, a characteristic region distribution calculating section that calculates respective spatial positions of the characteristic regions in the whole object based on respective positions of the characteristic regions, in each of the transmission-type images, which are selected in each of the transmission-type images, so as to calculate a spatial distribution of the characteristic regions in the whole object, and a three-dimensional image reconstructing section that, when reconstructing the three-dimensional image which shows the three-dimensional structure of the object and in which the densities of different levels are allocated to the whole object by integrating the transmission-type images, allocates the densities of different levels of the transmission-type images to respective positions, in the three-dimensional image, of the characteristic regions based on the spatial distribution of the characteristic regions in the whole object, so as to reconstruct the three-dimensional image in which a three-dimensional structure in each of the characteristic regions is shown.

A sixth embodiment of the present invention provides a computer readable medium storing thereon a three-dimensional image reconstructing program which causes a computer to function as a three-dimensional image reconstructing apparatus for reconstructing a three-dimensional image showing a three-dimensional structure of an object based on an image of the object which is obtained by image-capturing the object. The program causes the computer to function as an image-capturing section that captures a plurality of transmission-type images by transmitting an electron beam through the object from a plurality of different angles, where the transmission-type images each are represented by densities of different levels and include the object, and a infinitesimal region allocating section that divides, into a plurality of infinitesimal regions, a region within a predetermined thickness relating to the object, and reconstructs the three-dimensional image of the object by allocating a density of a certain level to each of the infinitesimal regions in compliance with the densities of different levels of the transmission-type images captured by the image-capturing section.

Here, all the necessary features of the present invention are not listed in the summary. The sub-combinations of the features may become the invention.

The present invention can reconstruct a three-dimensional image including not only morphological information indicating the outline of an object but also information indicating the internal structure of the object.

BRIEF DESCRIPTION OF THE DRAWINGS

FIGS. 7A to 7E are used to illustrate an exemplary operation performed by an enhancement processing section 120 relating to the embodiment of the present invention.

DESCRIPTION OF EXEMPLARY EMBODIMENTS

Hereinafter, one aspect of the present invention will be described through some embodiments. The embodiments do not limit the invention according to the claims, and all the combinations of the features described in the embodiments are not necessarily essential to means provided by aspects of the invention.

Figure 1:
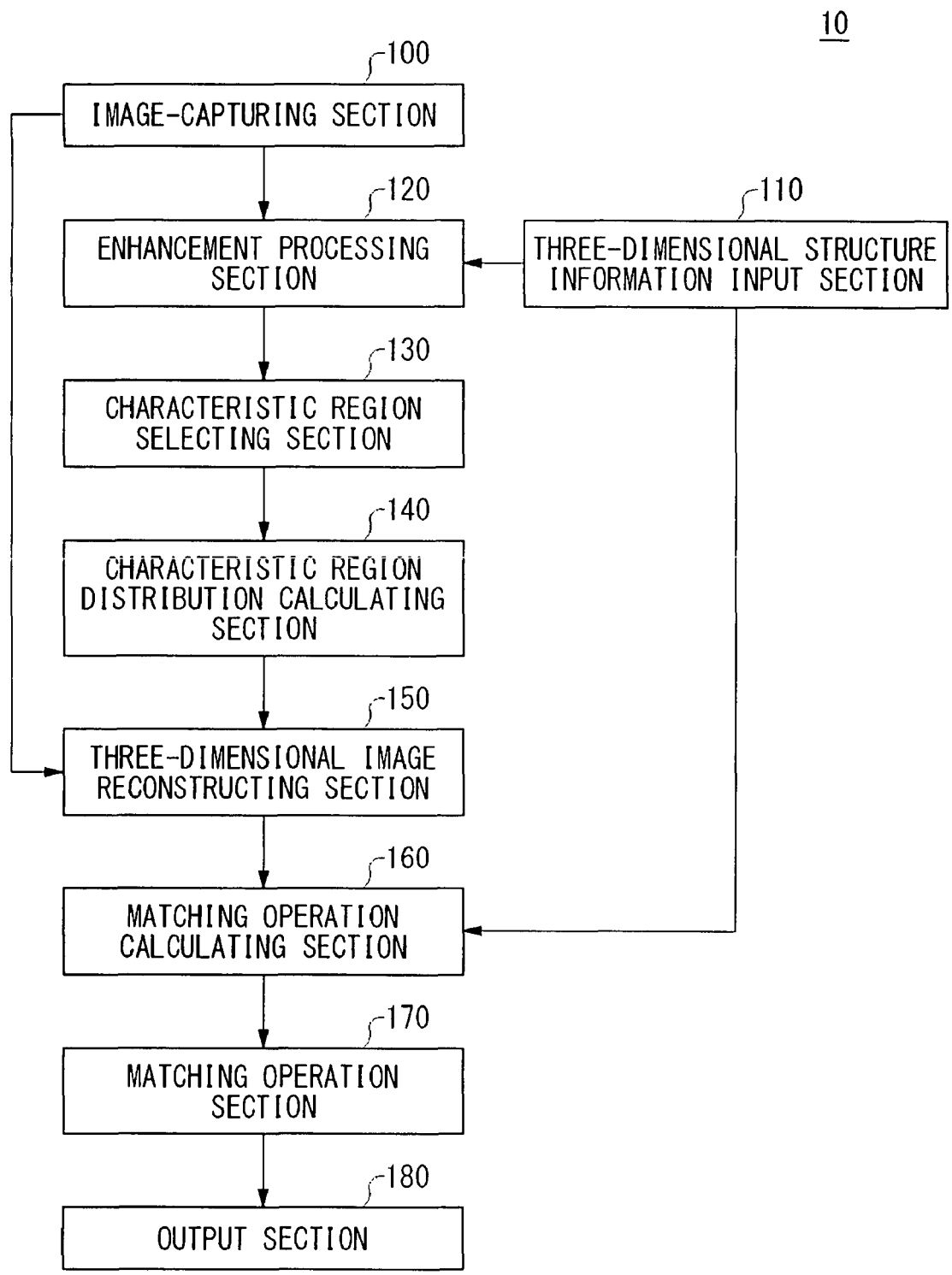
FIG. 1 is a block diagram illustrating an exemplary functional configuration of a three-dimensional image reconstructing apparatus 10 relating to an embodiment of the present invention.

FIG. 1 is a block diagram illustrating an exemplary functional configuration of a three-dimensional image reconstructing apparatus 10 relating to an embodiment of the present invention. The three-dimensional image reconstructing apparatus 10 reconstructs a three-dimensional image showing the three-dimensional structure of an object such as a protein of a cell, based on images of the object which are obtained by image-capturing the object.

The three-dimensional image reconstructing apparatus 10 relating to the embodiment of the present invention aims to reconstruct a three-dimensional image containing not only morphological information indicating the outline of the object but also information indicating the internal structure of the object. Also, the three-dimensional image reconstructing apparatus 10 relating to the embodiment of the present invention aims to achieve another object of reconstructing a highly accurate three-dimensional image based on a smaller number of images than a conventional three-dimensional image reconstructing apparatus.

The three-dimensional image reconstructing apparatus 10 includes therein an image-capturing section 100, a three-dimensional structure information input section 110, an enhancement processing section 120, a characteristic region selecting section 130, a characteristic region distribution calculating section 140, a three-dimensional image reconstructing section 150, a matching operation calculating section 160, a matching operation section 170, and an output section 180. The image-capturing section 100 may be a transmission electron microscope, for example. The image-capturing section 100 captures a plurality of transmission-type images each including an object by transmitting an electron beam through the object at a plurality of different angles. The captured transmission-type images show the object based on densities of different levels. Here, the image-capturing section 100 may capture a plurality of transmission-type images each including an object whose inside is stained by using, for example, a negative staining method or the like, or whose inside is not stained but which has a three-dimensional structure based on a density distribution. The image-capturing section 100 outputs the captured transmission-type images to the enhancement processing section 120 and three-dimensional image reconstructing section 150.

The three-dimensional structure information input section 110 receives an approximate three-dimensional structure of the object, based on a user's operation, for example. The three-dimensional structure information input section 110 outputs information indicating the received approximate three-dimensional structure, to the enhancement processing section 120 and matching operation calculating section 160. The enhancement processing section 120 performs an image processing operation to enhance the object in each of the transmission-type images captured by the image-capturing section 100 based on the approximate three-dimensional structure of the object which is received by the three-dimensional structure information input section 110. The enhancement processing section 120 outputs the transmission-type images after completing the image processing operation to enhance the object, to the characteristic region selecting section 130.

The characteristic region selecting section 130 selects a plurality of characteristic regions included in the object, in each of the transmission-type images received from the enhancement processing section 120. The characteristic region selecting section 130 outputs, to the characteristic region distribution calculating section 140, the transmission-type images and information specifying each of the characteristic regions selected in each of the transmission-type images, for example, the position, shape, size and the like of each characteristic region. The characteristic region distribution calculating section 140 receives, from the characteristic region selecting section 130, the transmission-type images and the information specifying each of the characteristic regions selected by the characteristic region selecting section 130 in each of the transmission-type images. Based on the positions of the characteristic regions selected in each of the transmission-type images, in the transmission-type image, the characteristic region distribution calculating section 140 calculates the respective spatial positions of the characteristic regions in the whole object, so as to calculate the spatial distribution of the characteristic regions in the whole object. The characteristic region distribution calculating section 140 outputs information indicating the calculated distribution of the characteristic regions to the three-dimensional image reconstructing section 150.

The three-dimensional image reconstructing section 150 reconstructs the three-dimensional structure of the object by integrating the transmission-type images received from the image-capturing section 100. Here, when reconstructing a three-dimensional image in which the densities of different levels are allocated to the whole object, the three-dimensional image reconstructing section 150 reconstructs a three-dimensional image in which the three-dimensional structure of each characteristic region is shown, by allocating the densities of different levels of the transmission-type images to the positions, in the three-dimensional image, of the characteristic regions, based on the spatial distribution of the characteristic regions in the whole object which is calculated by the characteristic region distribution calculating section 140. The three-dimensional image reconstructing section 150 outputs the reconstructed three-dimensional image to the matching operation calculating section 160.

The matching operation calculating section 160 calculates an image processing operation, by solving a simultaneous equation, to determine the densities of a three-dimensional structure, which is reconstructed by the three-dimensional image reconstructing section 150, of any of the characteristic regions selected by the characteristic region selecting section 130, which has a known three-dimensional structure, so that the densities of the three-dimensional structure of the characteristic region which has the known three-dimensional structure match the known three-dimensional structure. The matching operation calculating section 160 outputs the reconstructed three-dimensional image and information indicating the calculated image processing operation to the matching operation section 170. The matching operation section 170 performs the image processing operation calculated by the matching operation calculating section 160 on one or more of the characteristic regions selected by the characteristic region selecting section 130 which have an unknown three-dimensional structure, specifically on the densities of the three-dimensional images of such characteristic regions which are reconstructed by the three-dimensional image reconstructing section 150. The matching operation section 170 outputs the three-dimensional image which has been subjected to the image processing to the output section 1.80. The output section 180 may be, for example, a display apparatus such as an LCD panel or a storage apparatus such as a hard disk drive. The output section 180 outputs the three-dimensional image received from the matching operation section 170 to the outside, so as to provide a user with the three-dimensional image.

The three-dimensional image reconstructing apparatus 10 relating to the embodiment of the present invention can reconstruct a three-dimensional image in which the densities of different levels are allocated to the whole object, based on the spatial distribution of the characteristic regions in each of the transmission-type images obtained by image-capturing the object from a plurality of difference angles. With this configuration, the embodiment of the present invention can provide the user with a three-dimensional image including not only morphological information indicating the outline of the object having a three-dimensional structure but also information indicating the internal structure of the object, differently from a conventional three-dimensional image reconstructing apparatus.

The three-dimensional image reconstructing apparatus 10 relating to the embodiment of the present invention captures images of an object the inside of which is stained or the inside of which is not stained but which has a three-dimensional structure based on a density distribution by using a transmission electron microscope, and puts limitations on three-dimensional image reconstruction in accordance with the information which estimates the spatial position of a particular internal constituent within the object by way of a different method such as pattern recognition, for example. With this configuration, the three-dimensional image reconstructing apparatus 10 requires a significantly smaller number of inclined images which are captured by varying the angle formed between the specimen and image-capturing direction, when compared with a conventional three-dimensional image reconstructing apparatus which reconstructs a three-dimensional image only based on the combination of pieces of density information. As a result, the three-dimensional image reconstructing apparatus 10 relating to the embodiment of the present invention can reconstruct a three-dimensional image with it being possible to reduce the degree of destruction of the structure of the object which is caused by the image-capturing.

According to the above description with reference to FIG. 1, the matching operation calculating section 160 calculates the image processing operation to determine the densities of the three-dimensional structure of the characteristic region which has the known three-dimensional structure, so that the densities of the three-dimensional structure of the characteristic region which has the known three-dimensional structure match the known three-dimensional structure, based on the information indicating the approximate three-dimensional structure which is received by the three-dimensional structure information input section 110. Alternatively, however, the matching operation calculating section 160 may calculate the image processing operation based on, for example, information input by the user separately, which is different from the approximate three-dimensional structure used by the enhancement processing section 120.

Figure 2:
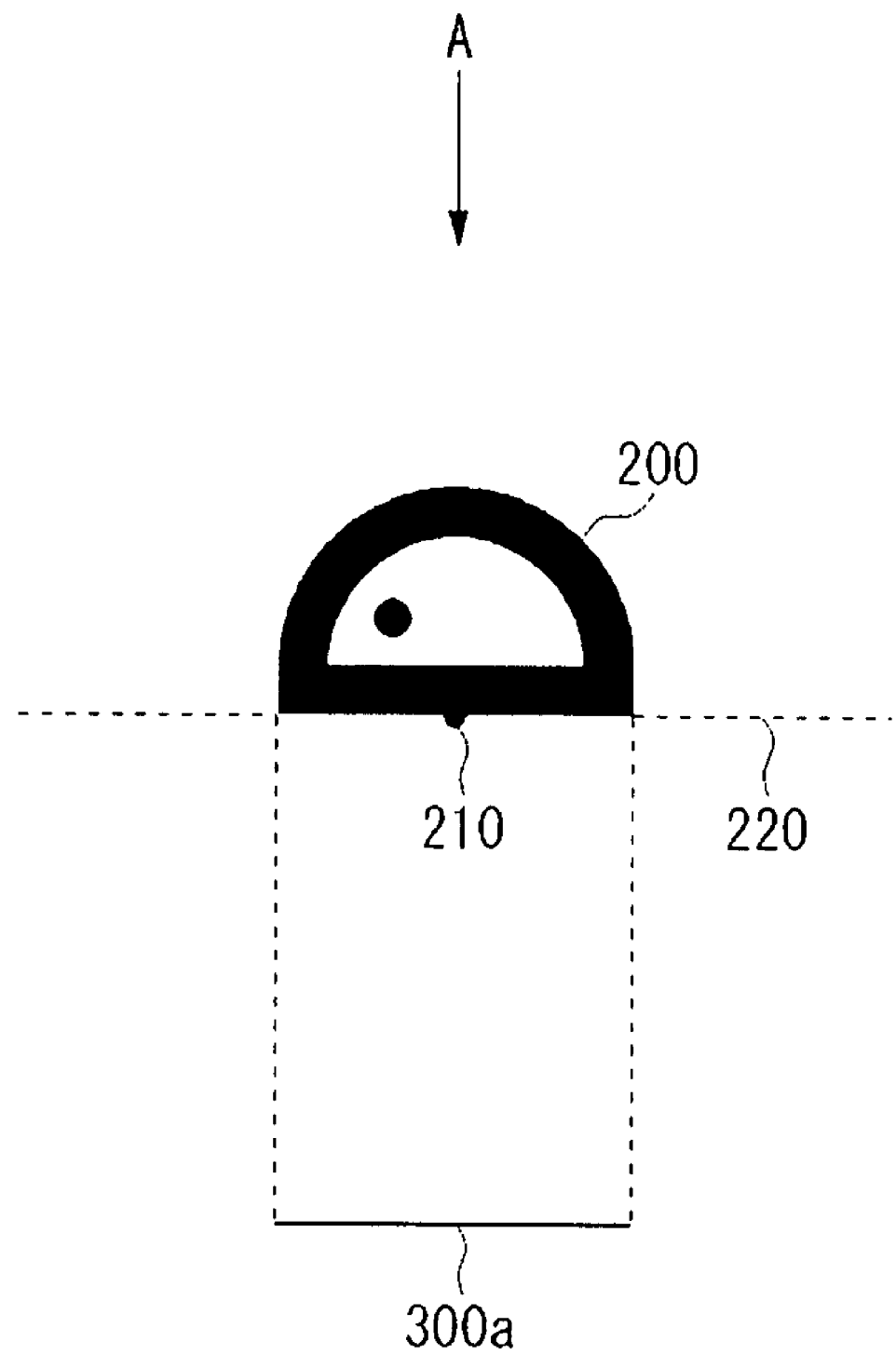
FIG. 2 illustrates a transmission-type image 300a which is a first example of a transmission-type image which is captured by an image-capturing section 100 relating to the embodiment of the present invention.
Figure 3:
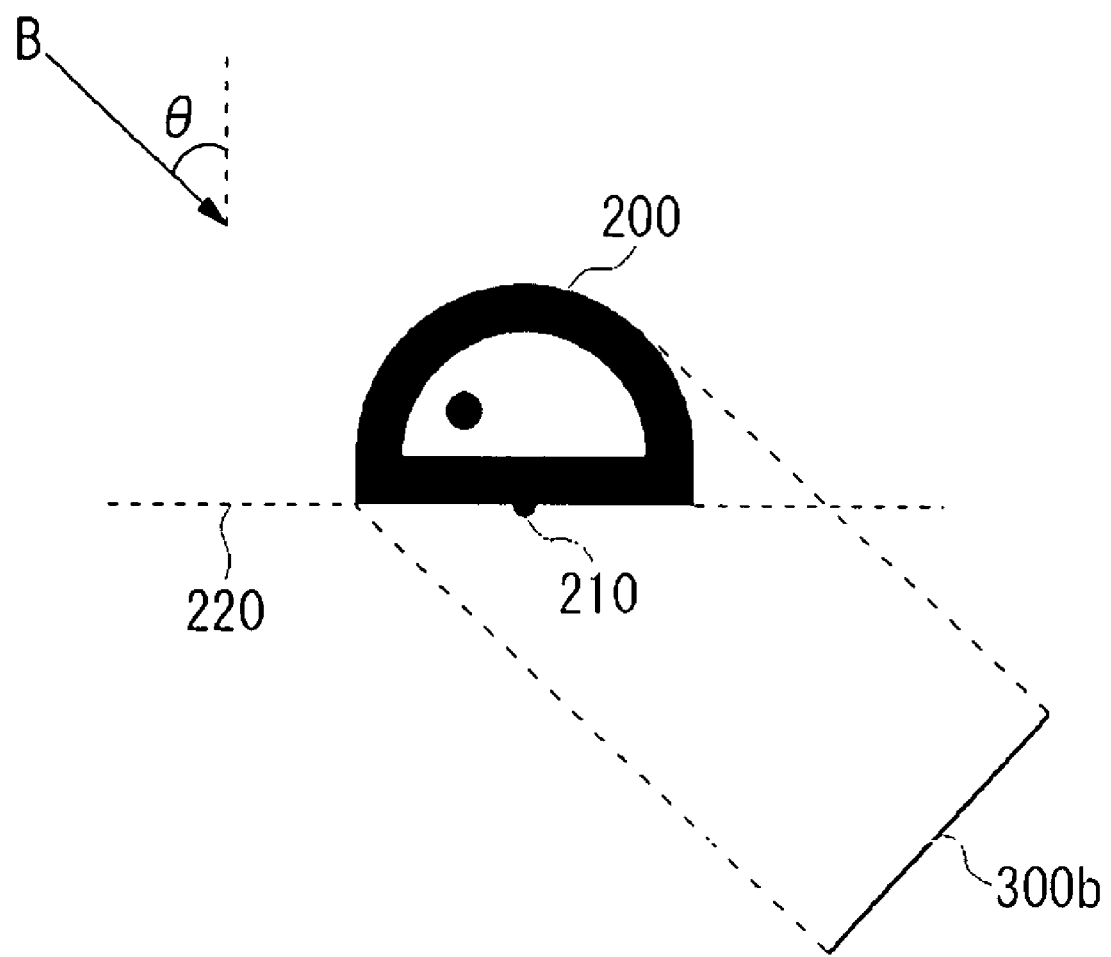
FIG. 3 illustrates a transmission-type image 300b which is a second example of the transmission-type image which is captured by the image-capturing section 100 relating to the embodiment of the present invention.
Figure 4:
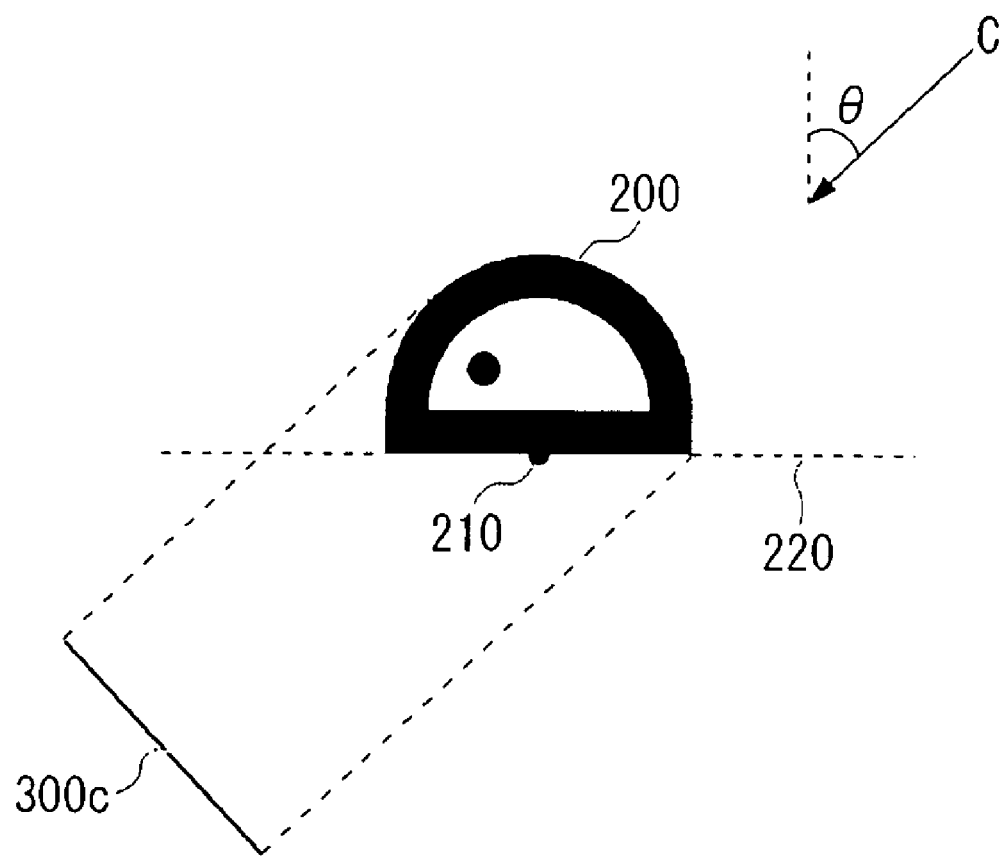
FIG. 4 illustrates a transmission-type image 300c which is a third example of the transmission-type image which is captured by the image-capturing section 100 relating to the embodiment of the present invention.

FIG. 2 illustrates a transmission-type image 300*a* which is a first example of a transmission-type image which is captured by the image-capturing section 100 relating to the embodiment of the present invention. FIG. 3 illustrates a transmission-type image 300*b* which is a second example of the transmission-type image which is captured by the image-capturing section 100 relating to the embodiment of the present invention. FIG. 4 illustrates a transmission-type image 300*c* which is a third example of the transmission-type image which is captured by the image-capturing section 100 relating to the embodiment of the present invention. The image-capturing section 100 captures images of an object 200 from at least three different angles. In the present embodiment, the image-capturing section 100 captures an image of the object 200 from the A direction, to output the transmission-type image 300*a*. The image-capturing section 100 captures an image of the object 200 from the B direction, to output the transmission-type image 300*b*. The image-capturing section 100 captures an image of the object 200 from the C direction, to output the transmission-type image 300*c*. Here, it is preferable that, as shown in FIGS. 3 and 4, the B and C directions each from the same angle (θ) with respect to the A direction. Also, the B and C directions may be set by rotating the A direction with respect to the same axis 210, or respectively by rotating the A direction with respect to different axes, for example, the axis 210 and an axis 220.

Figure 5:
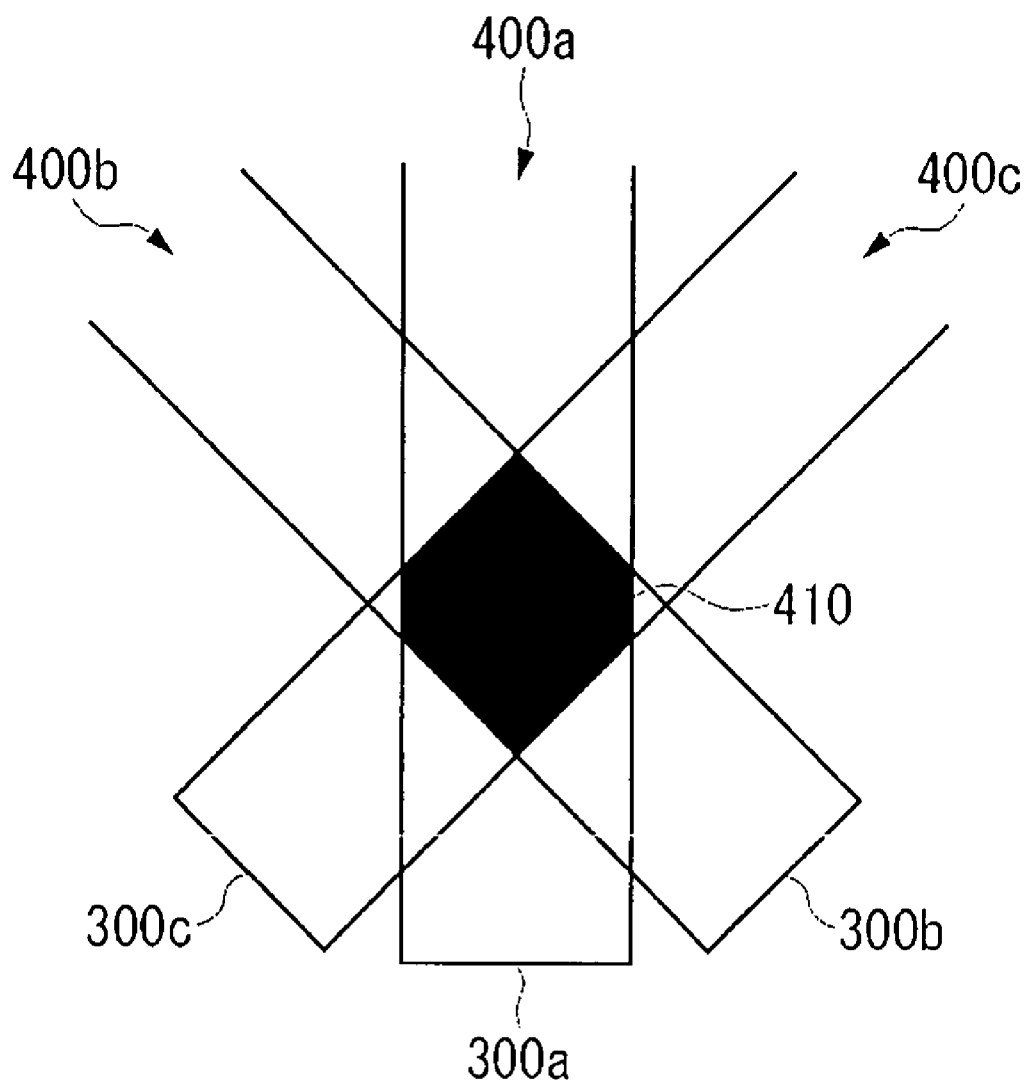
FIG. 5 illustrates, as an example, an operation of integrating a plurality of transmission-type images which is performed by a three-dimensional image reconstructing section 150 relating to the embodiment of the present invention.

FIG. 5 illustrates, as an example, an operation of integrating the transmission-type images which is performed by the three-dimensional image reconstructing section 150 relating to the embodiment of the present invention. The three-dimensional image reconstructing section 150 extends the transmission-type images captured by the image-capturing section 100 in the directions in which the transmission-type images are captured, to generate a plurality of pieces of density distribution information. The three-dimensional image reconstructing section 150 integrates the generated pieces of density distribution information in such a manner that the angular relation therebetween is maintained so as to be the same as the angular relation between the image-capturing directions for the transmission-type images corresponding to the pieces of density distribution information.

Specifically speaking, the three-dimensional image reconstructing section 150 extends, in the A direction, the transmission-type image 300*a* obtained by the image-capturing section 100 by image-capturing the object 200 in the A direction, so as to generate the density distribution information 400*a*. Similarly, the three-dimensional image reconstructing section 150 extends, in the B direction, the transmission-type image 300*b* obtained by the image-capturing section 100 by image-capturing the object 200 in the B direction, so as to generate the density distribution information 400*b*. Also, the three-dimensional image reconstructing section 150 extends, in the C direction, the transmission-type image 300*c* obtained by the image-capturing section 100 by image-capturing the object 200 in the C direction, so as to generate the density distribution information 400*c*. After this, the three-dimensional image reconstructing section 150 integrates the generated pieces of density distribution information 400*a*, 400*b* and 400*c* in Such a manner that the angular relation therebetween is maintained so as to be the same as the angular relation between the A, B and C directions. Note that FIG. 5 shows the cross-sections of the pieces of density distribution information which are cut along the plane including the A, B and C directions.

Here, the three-dimensional image reconstructing section 150 detects a region 410 which integrates all of the pieces of density distribution information, as a region in which the object 200 is present. However, the region 400 includes therein a region referred to as "a phantom" in which the object 200 is actually not present. Therefore, the three-dimensional image reconstructing section 150 can not reconstruct a highly accurate three-dimensional image showing the three-dimensional structure of the object 200 only by detecting the region 400.

Figure 6:
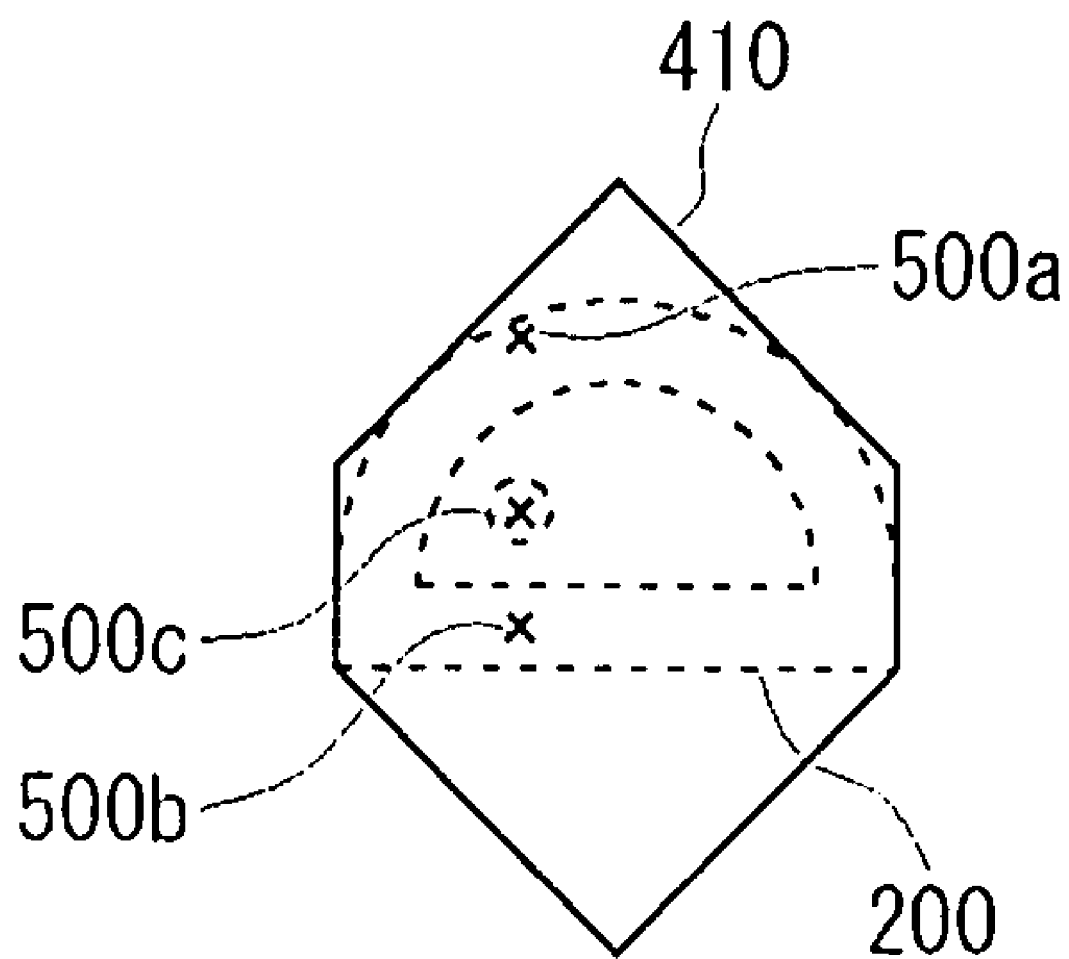
FIG. 6 illustrates, as an example, an operation of reconstructing a three-dimensional image which is performed by the three-dimensional image reconstructing section 150 relating to the embodiment of the present invention.

FIG. 6 illustrates, as an example, the operation of reconstructing the three-dimensional image which is performed by the three-dimensional image reconstructing section 150 relating to the embodiment of the present invention. The characteristic region selecting section 130 selects a plurality of characteristic regions in each of the transmission-type images. Specifically speaking, when the image-capturing section 100 captures the transmission-type images in such an order that the angle in which the image of the object is captured monotonically increases or decreases, the characteristic region selecting section 130 detects a region in a certain transmission-type image which corresponds to a characteristic region selected for a different transmission-type image which is captured before or after the certain transmission-type image. The characteristic region selecting section 130 may use, for example, a known image processing technique referred to as cross-correlation processing in order to detect characteristic regions which correspond to each other and are respectively included in different transmission-type images. For example, the characteristic region selecting section 130 may select, as a characteristic region in a transmission-type image, a region which shows a larger difference in density level than other regions in the same transmission-type image. The characteristic region selecting section 130 performs the above-mentioned operation to detect corresponding characteristic regions between two transmission-type images which are captured successively. The characteristic region selecting section 130 sequentially performs this operation on each combination of two transmission-type images which are captured successively. In this way, the characteristic region selecting section 130 traces each of the characteristic regions among the captured transmission-type images.

Subsequently, the characteristic region distribution calculating section 140 calculates the spatial position, in the whole object, of each of the characteristic regions selected by the characteristic region selecting section 130, based on the position of each characteristic region in a corresponding one of the transmission-type images. Specifically speaking, the characteristic region distribution calculating section 140 uses a known method referred to as stereo measurement, according to which information regarding the height of a single point is calculated based on the parallax observed when the single point is measured from different angles. Using stereo measurement, the characteristic region distribution calculating section 140 calculates the spatial position, in the whole object, of each characteristic region, by detecting a difference in position of each characteristic region between the transmission-type images which are captured from a plurality of different angles. Referring to FIG. 6, for example, the characteristic region distribution calculating section 140 calculates the spatial positions of the characteristic regions as points 500a, 500b and 500c. Here, it is assumed that the points 500a, 500b and 500c are seen as a single point when seen from the A direction shown in FIG. 2. It should be noted that although only three characteristic regions are shown in FIG. 6 to simplify the explanation, the number of characteristic regions whose spatial positions are calculated by the characteristic region distribution calculating section 140 is not limited to three. To reconstruct a more accurate three-dimensional image of the object 200, it is preferable that the spatial positions of a larger number of characteristic regions are calculated.

The characteristic region distribution calculating section 140 may calculate the spatial position, in the whole object, of each characteristic region, with reference to the position of the barycenter of each characteristic region. Alternatively, the characteristic region distribution calculating section 140 may calculate the spatial position, in the whole object, of each characteristic region, with reference to the position, in a corresponding one of the transmission-type images, of the outline of the object which is included in each characteristic region. In many cases, a-partial image, in a transmission-type image, which shows the outline of an object is more distinctive than other partial images. Therefore, by using the position of the outline of the object, the characteristic region distribution calculating section 140 can highly accurately calculate the difference in position of the characteristic region. As a result, the characteristic region distribution calculating section 140 can highly accurately calculate the spatial position of each of the characteristic regions, which enables a more accurate three-dimensional image of the object to be reconstructed.

The three-dimensional image reconstructing section 150 reconstructs the three-dimensional image of the object 200 based on the region 410 in which the object 200 is present, which is detected based on the pieces of density distribution information obtained by extending the captured transmission-type images in the respective image-capturing directions and the respective spatial positions of the characteristic regions which are calculated by the characteristic region distribution calculating section 140. Specifically speaking, the three-dimensional image reconstructing section 150 assumes that at least a portion of the object 200 is present, in the region 410, in the vicinity of each of the points 500a, 500b and 500c. Therefore, the three-dimensional image reconstructing section 150 evenly allocates the density levels in the whole region 410 to the vicinities of the points 500a, 500b and 500c. In this way, the three-dimensional image reconstructing section 150 reconstructs a three-dimensional image in which the three-dimensional structure of each of the characteristic regions is shown. According to the present embodiment, the points 500a, 500b and 500c, which indicate the spatial positions of the characteristic regions, are perceived as a single point when the object 200 is seen along the A direction. Therefore, if only the transmission-type image 300a is used, it can not be judged whether the number of characteristic regions present in the object 200 is one or three. According to the three-dimensional image reconstructing apparatus 10, however, the respective spatial positions of the characteristic regions are calculated with reference to the transmission-type images which are obtained by image-capturing the object from different angles, such as the A, B and C directions. Therefore, the three-dimensional image reconstructing apparatus 10 can detect that the points 500a, 500b and 500c are individually present in the object 200. As a result, the three-dimensional image reconstructing apparatus 10 can use the information indicating the internal structure of the object 200, which is obtained in the above-described manner, to reconstruct the three-dimensional image in which the densities of different levels are allocated to the whole object 200.

The three-dimensional image reconstructing apparatus 10 relating to the embodiment of the present invention can reconstruct the three-dimensional image of the object, based not only on the region which is detected by extending and then integrating the transmission-type images, but also on the spatial positions of the characteristic regions which are calculated by using stereo measurement or the like. With this configuration, the three-dimensional image reconstructing apparatus 10 can obtain more pieces of information from the transmission-type images to reconstruct the three-dimensional image of the object, when compared to a case where the three-dimensional image of the object is reconstructed based only on the region which is detected by extending and integrating the transmission-type images, or a case where the three-dimensional image of the object is reconstructed based further on the morphological information indicating the outline of the object. Which is to say, the three-dimensional image reconstructing apparatus 10 can reconstruct the three-dimensional image by using a smaller number of transmission-type images than a conventional three-dimensional image reconstructing apparatus. As a result, the three-dimensional image reconstructing apparatus 10 can reconstruct a highly accurate three-dimensional image with it being possible to reduce the degree of the destruction of the structure of the object which is caused by the electron beam transmitted through the object to capture the transmission-type images. This effect enables the three-dimensional image reconstructing apparatus 10 to reconstruct a highly accurate three-dimensional image, even when the object has such an unstable structure that the structure of the object is varied while many images of the object are captured.

FIGS. 7A to 7E are used to illustrate an exemplary operation preformed by the enhancement processing section 120 relating to the embodiment of the present invention. The enhancement processing section 120 performs image processing on the transmission-type images captured by the image-capturing section 100, based on the approximate three-dimensional structure of the object which is received by the three-dimensional structure information input section 110, by using a known technology such as morphological filter processing, for example, so as to enhance the object in the transmission-type images. Here, the approximate three-dimensional structure of the object may be input by the user, and indicate, for example, information specifying the thickness of the object when the object is shaped like a line. The following describes an example of the image processing preformed by the enhancement processing section 120 with reference to FIGS. 7A to 7E.

FIG. 7A illustrates the relation between the position and luminance within a transmission-type image captured by the image-capturing section 100, along a certain line. Note that the transmission-type image is a gray scale image expressed in 256 levels in the present embodiment. FIG. 7B illustrates the approximate three-dimensional structure of the object which is received by the three-dimensional structure information input section 110. According to the present embodiment, the object has a structure shaped like a line. FIG. 7B shows the typical thickness T of the object.

The enhancement processing section 120 detects a portion of the captured transmission-type image in which the object is not present, that is to say, background noise based on the transmission-type image and the received approximate three-dimensional structure of the object. Specifically speaking, the enhancement processing section 120 detects a region of the captured transmission-type image which shows a structure whose thickness is different from the typical thickness T of the structure of the object by a value equal to or lower than a reference value determined in advance by the user or the like. In other words, the enhancement processing section 120 detects regions 600, 610 and 620 shown in FIG. 7A, as regions each showing a portion of the object. Subsequently, the enhancement processing section 120 generates a background image by removing the portions detected as the regions showing a portion of the object from the captured transmission-type image. FIG. 7C shows the relation between the position and luminance in the background image generated by the enhancement processing section 120 in the above-described manner, along the same line as used in FIG. 7A.

The enhancement processing section 120 then generates an object image which shows the object, by subtracting the generated background image from the captured transmission-type image. Specifically speaking, the enhancement processing section 120 generates the object image by subtracting the luminance of each of the pixels of the background image from the luminance of a corresponding one of the pixels of the captured transmission-type image. FIG. 7D shows the relation between the position and luminance in the object image generated by the enhancement processing section 120 in the above-described manner, along the same line as used in FIG. 7A.

Subsequently, the enhancement processing section 120 performs an operation on the generated object image to obtain a binary image. Specifically speaking, the enhancement processing section 120 enhances the contrast of each region, in the generated object image, showing the object by setting the maximum value of the luminance of each region at, for example a level 255. In this way, the enhancement processing section 120 generates an object enhanced image. FIG. 7E shows the relation between the position and luminance in the object enhanced image generated by the enhancement processing section 120 in the above-described manner, along the same line as used in FIG. 7A.

The enhancement processing section 120 generates the object enhanced image by performing, on the captured transmission-type image, the image processing to enhance the object in the above-described manner, and outputs the generated image to the characteristic region selecting section 130 and three-dimensional image reconstructing section 1 50.

The three-dimensional image reconstructing apparatus 10 relating to the embodiment of the present invention can enhance the object by removing the background noise which is not the density information indicating the object, from the density information of the captured transmission-type image. With this configuration, the three-dimensional image reconstructing apparatus 10 can reconstruct a more accurate three-dimensional image of the object.

Figure 8A:
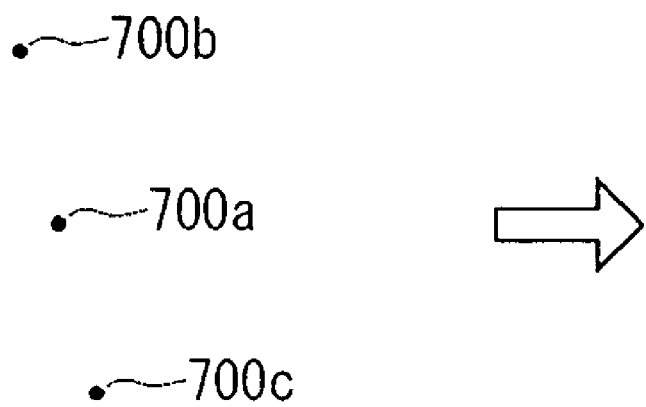
FIGS. 8A and 8B are used to illustrate an exemplary operation performed by a matching operation calculating section 160 relating to the embodiment of the present invention.
Figure 8B:
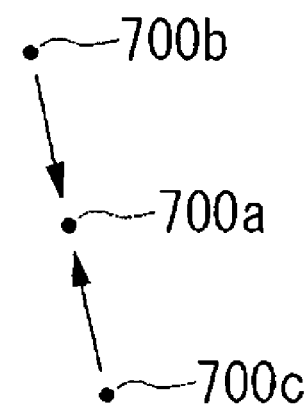

FIGS. 8A and 8B are used to illustrate an exemplary operation performed by the matching operation calculating section 160 relating to the embodiment of the present invention. In the present embodiment, the densities of the three-dimensional image of a certain characteristic region which is reconstructed by the three-dimensional image reconstructing section 150 includes three points 700a, 700b and 700c as shown in FIG. 8A. Here, it is assumed that the known three-dimensional structure which is received by, for example, the three-dimensional structure information input section 110 indicates that the characteristic region includes a single point only. In other words, blurring is found in the densities of the reconstructed three-dimensional image of the characteristic region in the present embodiment.

In this case, the matching operation calculating section 160 calculates an image processing operation to determine the densities of the reconstructed three-dimensional image of the characteristic region, so that the densities of the reconstructed three-dimensional image of the characteristic region match the known three-dimensional structure. Specifically speaking, the matching operation calculating section 160 calculates an image processing operation to determine the positions of the points 700*b* and 700*c* so that the positions of the points 700*b* and 700*c* match the position of the point 700*a* as shown in FIG. 8B, in order to determine the densities of the three-dimensional image so that the densities of the three-dimensional image match the known three-dimensional structure with reference to the point 700*a*. Here, the image processing operation to be obtained by the calculation may include, for example, a variety of image processing operations such as enlarging, shrinking, rotating, modifying and the like, to be performed on at least part of the characteristic region. The matching operation section 170 performs the image processing operation calculated by the matching operation calculating section 160, on the densities of the three-dimensional image reconstructed in another characteristic region which shows an unknown three-dimensional structure, where such a characteristic region is different from the characteristic region shown in FIGS. 8A and 8B.

When an object is image-captured by using a transmission electron microscope from different angles, factors such as apparatus limitations and characteristics of a specimen to be image-captured may put limitations on the range of the image-capturing angles. Specifically speaking, the angle θ shown in FIGS. 3 and 4 is limited to take a range of approximately −60° and +60°. This limitation poses a problem since no projection images of the object can be obtained from the angles outside this range. To be specific, the reconstructed three-dimensional image should originally have the same resolution in terms of a cross-sectional surface in every direction, but for the above-described reason, only the resolution in the height direction is degraded. Therefore, all the cross-sectional images of the reconstructed three-dimensional image may be extended in one direction, or the reconstructed three-dimensional image may represent a wrong structure or shape. As a result, a three-dimensional image representing the three-dimensional structure of the object with a sufficiently high resolution may not be reconstructed. The three-dimensional image reconstructing apparatus 10 relating to the embodiment of the present invention, however, can calculate an image processing operation to determine the densities of a three-dimensional image of a characteristic region which has a known three-dimensional structure, so that the densities of the three-dimensional image of the characteristic region which has the known three-dimensional structure match the known three-dimensional structure, and perform the calculated image processing operation onto the densities of the three-dimensional structure of another characteristic region which shows the unknown three-dimensional structure. With this configuration, the three-dimensional image reconstructing apparatus 10 can correct the densities of the whole object in the reconstructed three-dimensional image, thereby being capable of outputting a high-quality three-dimensional image representing the three-dimensional structure of the object with a higher resolution.

Figure 9:
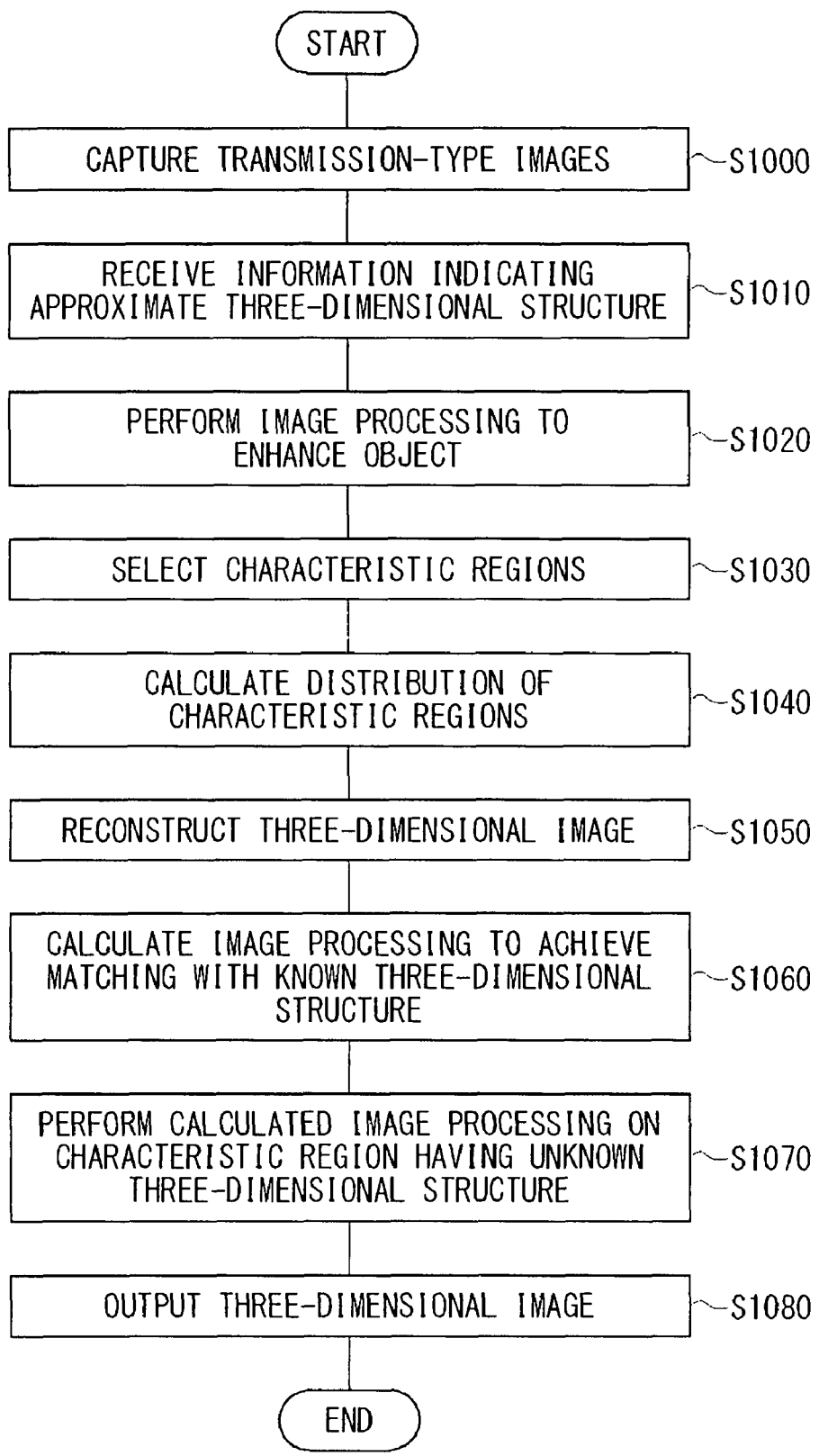
FIG. 9 is a flow chart illustrating an exemplary flow of processes making up a three-dimensional image reconstructing method which is conducted by using the three-dimensional image reconstructing apparatus 10 relating to the embodiment of the present invention.

FIG. 9 is a flow chart illustrating an exemplary flow of processes making up a three-dimensional image reconstructing method which is conducted by using the three-dimensional image reconstructing apparatus 10 relating to the embodiment of the present invention. To start with, the image-capturing section 100 captures a plurality of transmission-type images which include an object and are represented using densities of different levels, by transmitting an electron beam through the object from different angles (step S1000). Subsequently, the three-dimensional structure information input section 110 receives information indicating the approximate three-dimensional structure of the object (step S1010). After this, the enhancement processing section 120 performs an image processing operation on each of the captured transmission-type images to enhance the object, based on the received approximate three-dimensional structure (step S1020).

Subsequently, the characteristic region selecting section 130 selects a plurality of characteristic regions included in the object which is enhanced by the enhancement processing section 120, in each of the transmission-type images (step S1030). Following this, the characteristic region distribution calculating section 140 calculates the respective spatial positions of the characteristic regions in the whole object, based on the positions of the characteristic regions in each of the transmission-type images, so as to calculate the spatial distribution of the characteristic regions in the whole object (step S1040). Subsequently, the three-dimensional image reconstructing section 150 reconstructs the three-dimensional structure of the object by integrating the transmission-type images (step S1050). Here, the three-dimensional image reconstructing section 150 reconstructs the three-dimensional image in which the densities of different levels are allocated to the whole object, by allocating the densities of different levels shown by the transmission-type images to the respective positions of the characteristic regions based on the spatial distribution of the characteristic regions in the whole region so as to reconstruct the three-dimensional image in which the three-dimensional structure of each of the characteristic regions is shown.

After this, the matching operation calculating section 160 calculates an image processing operation to determine the densities of the reconstructed three-dimensional structure of any of the characteristic regions which has a known three-dimensional structure, so that the densities of the reconstructed three-dimensional structure of the characteristic region which has the known three-dimensional structure match the known three-dimensional structure (step S1060). Subsequently, the matching operation section 170 performs the image processing operation calculated by the matching operation calculating section 160 on the densities of the reconstructed three-dimensional image of each one of the characteristic regions which has an unknown three-dimensional structure (step S1070). The output section 180 outputs the three-dimensional image on which the image processing has been performed by the matching operation section 170 to the outside, thereby providing the three-dimensional image to the user (step S1080).

Figure 10:
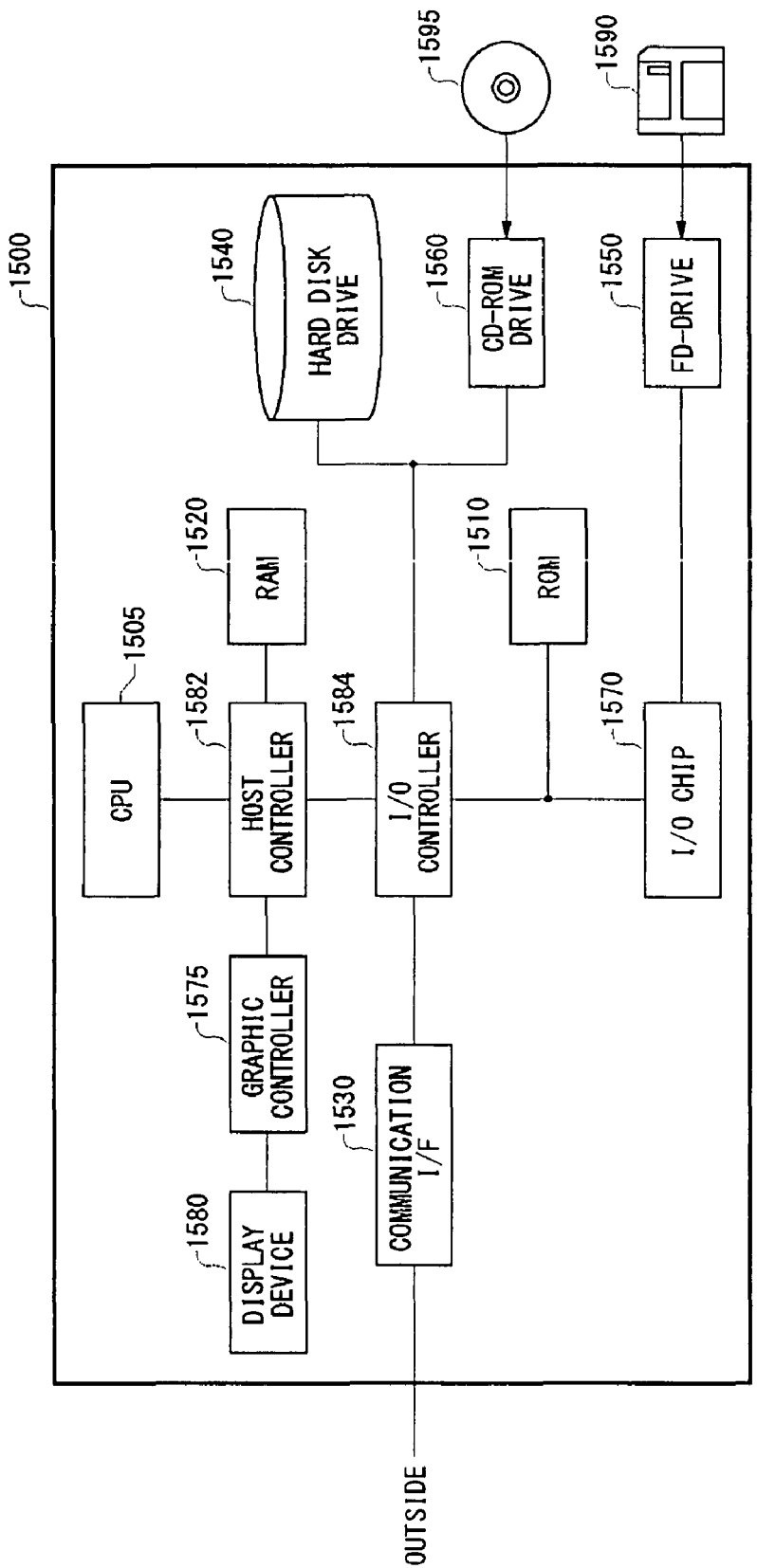
FIG. 10 is a block diagram illustrating an exemplary hardware configuration of a computer 1500 relating to the embodiment of the present invention.

FIG. 10 is a block diagram illustrating an exemplary hardware configuration of a computer 1500 relating to an embodiment of the present invention. The computer 1500 relating to the embodiment of the present invention is constituted by a CPU surrounding section, an input/output (I/O) section and a legacy I/O section. The CPU surrounding section includes a CPU 1505, a RAM 1520, a graphic controller 1575, and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon image data generated by the CPU 1505 or the like.

The I/O controller 1584 connects, to the host controller 1582, the communication interface 1530, hard disk drive 1540 and CD-ROM drive 1560 which are I/O devices operating at a relatively high rate. The communication interface 1530 communicates with a different device via a network. The hard disk drive 1540 stores thereon programs and data to be used by the CPU 1505 provided in the computer 1500. The CD-ROM drive 1560 reads programs and data from a CR-ROM 1595, and supplies the read programs and data to the hard disk drive 1540 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the computer 1500 at the start up, programs unique to the hardware of the computer 1500, and the like. The flexible disk drive 1550 reads programs and data from a flexible disk 1590, and supplies the read programs and data to the hard disk drive 1540 via the RAM 1520. The I/O chip 1570 is used to connect a variety of I/O devices such as the flexible disk drive 1550 via, for example, a parallel port, a serial port, a keyboard port, a mouse port or the like.

A three-dimensional image reconstructing program to be supplied to the hard disk drive 1540 via the RAM 1520 is provided by a user in a state of being stored on a recording medium such as the flexible disk 1590, CD-ROM 1595 and an IC card. The three-dimensional image reconstructing program is read from the recording medium, installed via the RAM 1520 in the hard disk drive 1540 in the computer 1500, and executed by the CPU 1505. The three-dimensional image reconstructing program to be installed in and thus executed by the computer 1500 causes the CPU 1505 and the like to operate the computer 1500 as the three-dimensional image reconstructing apparatus 10 described with reference to FIGS. 1 to 9.

The above-mentioned program may be stored on an external storage medium. Such a storage medium includes the flexible disk 1590, CD-ROM 1595, an optical storage medium such as a DVD and a PD, a magnet optical storage medium such as an MD, a tape medium, and a semiconductor memory such as an IC card. The storage medium may be a storage apparatus such as a hard disk and RAM which is provided in a server system connected to a dedicated communication network or the Internet, and the program may be provided to the computer 1500 via the network.

Figure 11:
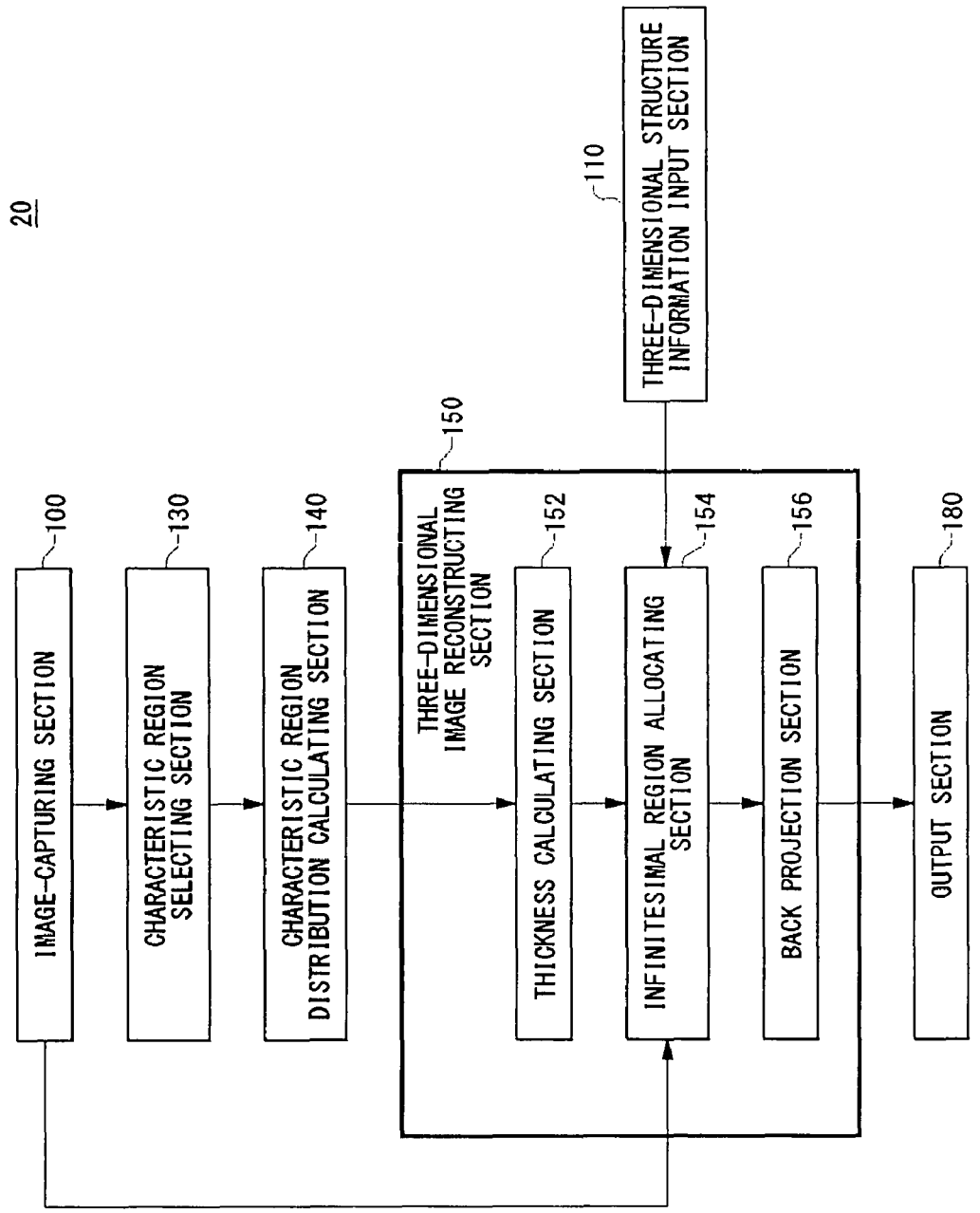
FIG. 11 is a block diagram illustrating an exemplary functional configuration of a three-dimensional image reconstructing apparatus 20 relating to a different embodiment of the present invention.

FIG. 11 is a block diagram illustrating an exemplary functional configuration of a three-dimensional image reconstructing apparatus 20 relating to a different embodiment of the present invention. The three-dimensional image reconstructing apparatus 20 includes therein the image-capturing section 100, three-dimensional structure information input section 110, characteristic region selecting section 130, characteristic region distribution calculating section 140, three-dimensional image reconstructing section 150, and output section 180. The three-dimensional image reconstructing section 150 therein includes a thickness calculating section 152, a infinitesimal region allocating section 154, and a back projection section 156.

The image-capturing section 100 has the same configuration and function as the image-capturing section 100 of the three-dimensional image reconstructing apparatus 10. The image-capturing section 100 image-captures an object from different angles, to obtain a plurality of transmission-type images, and outputs the transmission-type images to the characteristic region selecting section 130 and thickness calculating section 152. The three-dimensional structure information input section 110 receives information indicating the known facts about the three-dimensional structure of the object in accordance with a user's operation or the like. The three-dimensional structure information input section 110 outputs the received information indicating the approximate three-dimensional structure to the infinitesimal region allocating section 154.

The characteristic region selecting section 130 selects a plurality of characteristic regions included in the object, in each of the transmission-type images received from the image-capturing section 100. The characteristic region selecting section 130 outputs, to the characteristic region distribution calculating section 140, the transmission-type images and information specifying each of the characteristic regions selected in each of the transmission-type images, for example, the position, shape, size and the like of each characteristic region. The characteristic region distribution calculating section 140 receives, from the characteristic region selecting section 130, the transmission-type images and the information specifying each of the characteristic regions selected by the characteristic region selecting section 130 in each of the transmission-type images. The characteristic region distribution calculating section 140 calculates the respective spatial positions of the characteristic regions in the whole object based on the positions of the characteristic regions selected for each of the transmission-type images, in each transmission-type image, so as to calculate the spatial distribution of the characteristic regions in the whole object. The characteristic region distribution calculating section 140 outputs information indicating the calculated distribution of the characteristic regions to the thickness calculating section 152.

The thickness calculating section 152 calculates the thickness of the object in a direction in which the electron beam is transmitted through the object, based on the spatial distribution of the characteristic regions which is calculated by the characteristic region distribution calculating section 140. The thickness calculating section 152 outputs the spatial distribution of the characteristic regions and the calculated thickness to the infinitesimal region allocating section 154.

The infinitesimal region allocating section 154 divides, into a plurality of infinitesimal regions, a region of the object along the thickness calculated by the thickness calculating section 152. The infinitesimal region allocating section 154 reconstructs a three-dimensional image by allocating a density of a particular level to each of the infinitesimal regions in compliance with the densities of different levels of the transmission-type images captured by the image-capturing section 100. In this case, the infinitesimal region allocating section 154 divides each of the transmission-type images into a plurality of infinitesimal regions in correspondence with the infinitesimal regions making up the region of the object along the thickness. Furthermore, the infinitesimal region allocating section 154 allocates, to each of the infinitesimal regions of the transmission-type image, an integral value determined in proportion to the corresponding density. The infinitesimal region allocating section 154 allocates binary values each indicating a density to the infinitesimal regions making up the region of the object along the thickness, in such a manner that the total value of binary values, each indicating a density, which are allocated to some of the infinitesimal regions along the thickness which are grouped together in correspondence with the angle in which the transmission-type image is captured becomes equal to an integral value representing the density of a corresponding one of the infinitesimal regions of the transmission-type image. In the similar manner, the infinitesimal region allocating section 154 allocates binary values each indicating a density to the infinitesimal regions making up the region along each thickness direction of the whole object, to obtain the density distribution of the whole object. The infinitesimal region allocating section 154 supplies the obtained density distribution to the back projection section 156.

The back projection section 156 reconstructs a three-dimensional image of an object 202 by allocating the densities of different levels of the transmission-type images onto the obtained density distribution of the object 202. The back projection section 156 outputs the reconstructed three-dimensional image to the output section 180.

Figure 12:
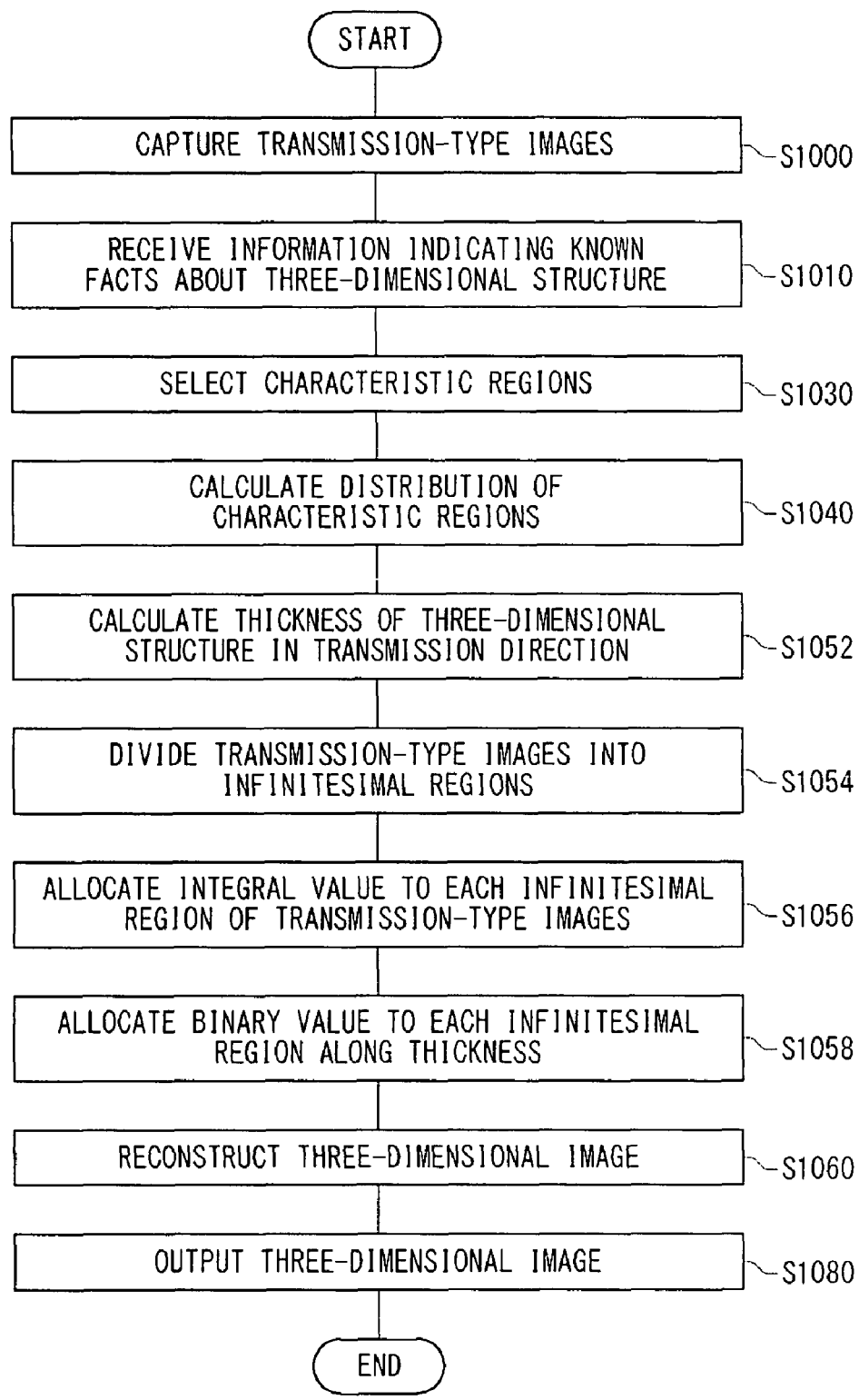
FIG. 12 is a flow chart illustrating an exemplary flow of processes making up a three-dimensional image reconstructing method which is conducted by using the three-dimensional image reconstructing apparatus 20 relating to the different embodiment of the present invention.
Figure 13:
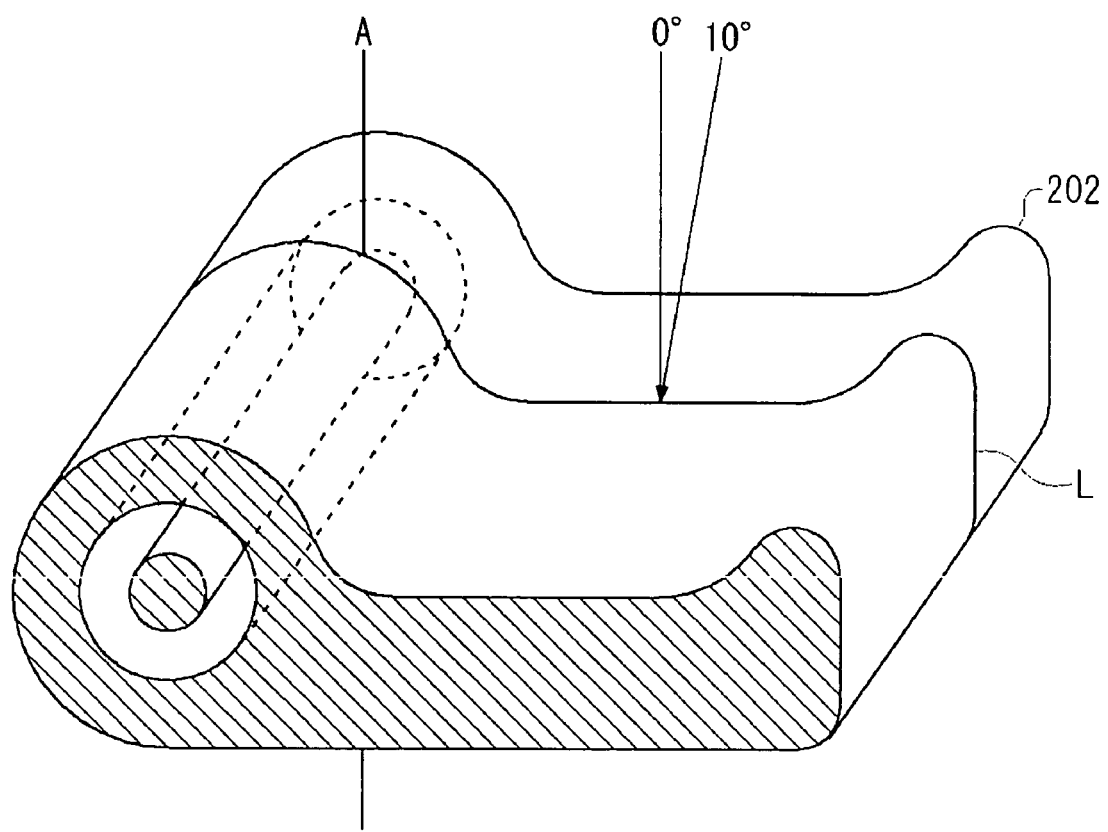
FIG. 13 schematically illustrates an object 202 an image of which is captured by the image-capturing section 100 relating to the different embodiment of the present invention.
Figure 14A:
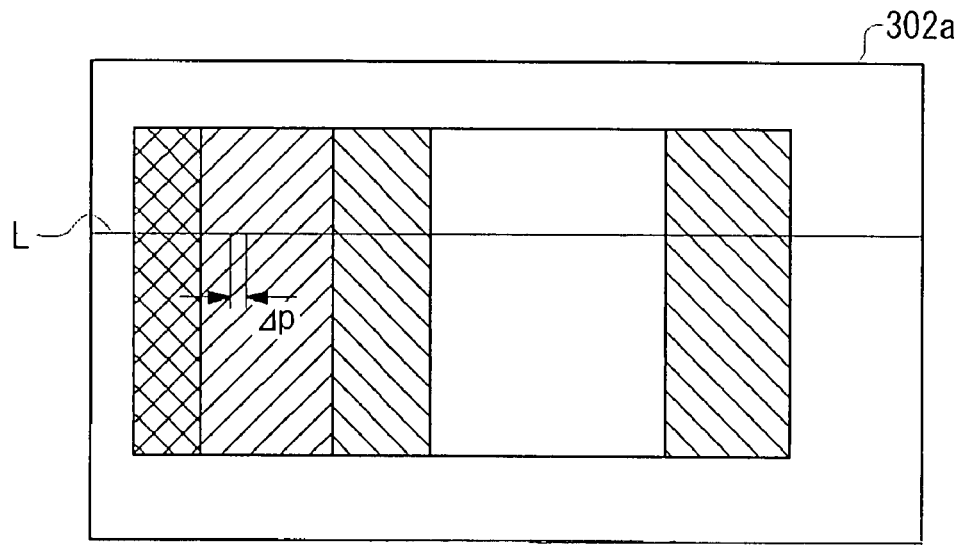
FIGS. 14A and 14B illustrate transmission-type images 302a and 302b which are captured by the image-capturing section 100 relating to the different embodiment of the present invention.
Figure 14B:
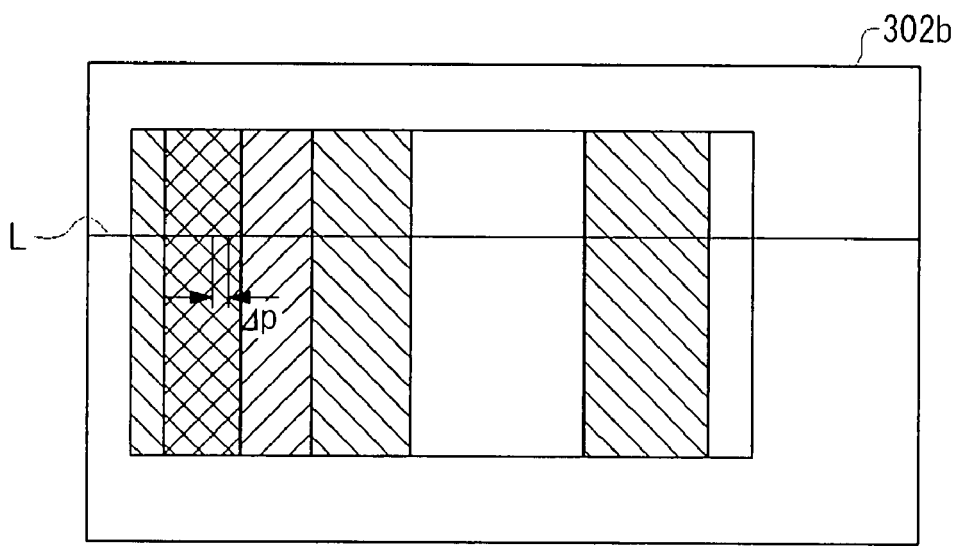

FIG. 12 is a flow chart illustrating an exemplary flow of processes making up a three-dimensional image reconstructing method which is conducted by using the three-dimensional image reconstructing apparatus 20 relating to the different embodiment of the present invention. FIG. 13 schematically illustrates an object 202 which is image-captured by the image-capturing section 100 relating to the different embodiment of the present invention. FIGS. 14A and 14B illustrate transmission-type images 302a and 302b which are captured by the image-capturing section 100 relating to the different embodiment of the present invention. Here, the step S1052 and subsequent steps of the flow chart shown in FIG. 12 are described with reference to FIGS. 15 to 17, in addition to FIGS. 13 and 14.

As shown in FIG. 13, the image-capturing section 100 captures the transmission-type image 302a including the object 202 shown in FIG. 14A by transmitting an electron beam through the object 202 from a certain angle (0°) (step S1000). Also, the image-capturing section 100 captures the transmission-type image 302b including the object 202 shown in FIG. 14B by transmitting an electron beam through the object 202 from a different angle (10°) with respect to a particular plane (step S1000). In the same manner, the image-capturing section 100 captures transmission-type images by varying, in units Of 100, the angle formed between the particular plane of the object 202 and the direction in which the electron beam is transmitted through the object 202. To simplify the description, not-illustrated transmission-type images (i.e. other than the transmission-type images 302a and 302b) are not wholly explained in the following.

After this, the three-dimensional structure information input section 110 receives the information indicating the known facts about the object 202 (step S1010). For example, when it is known that the object 202 has a fiber-like internal structure, the three-dimensional structure information input section 110 receives information from the user which indicates the length, thickness and the like of the fiber-like structure. Subsequently, the characteristic region selecting section 130 selects the characteristic regions included in the object 202, in each of the transmission-type images 302a and 302b (step S1030). Following this, the characteristic region distribution calculating section 140 calculates the respective spatial positions, in the whole object 202, of the characteristic regions, based on the positions, in each of the transmission-type images 302a and 302b, of the characteristic regions selected in each of the transmission-type images 302a and 302b, to calculate the spatial distribution of the characteristic regions in the whole object 202 (step S1040). Here, the steps S1010, S1030 and S1040 are the same as the corresponding operations performed by the three-dimensional image reconstructing apparatus 10 described with reference to FIGS. 1 to 10.

Figure 15:
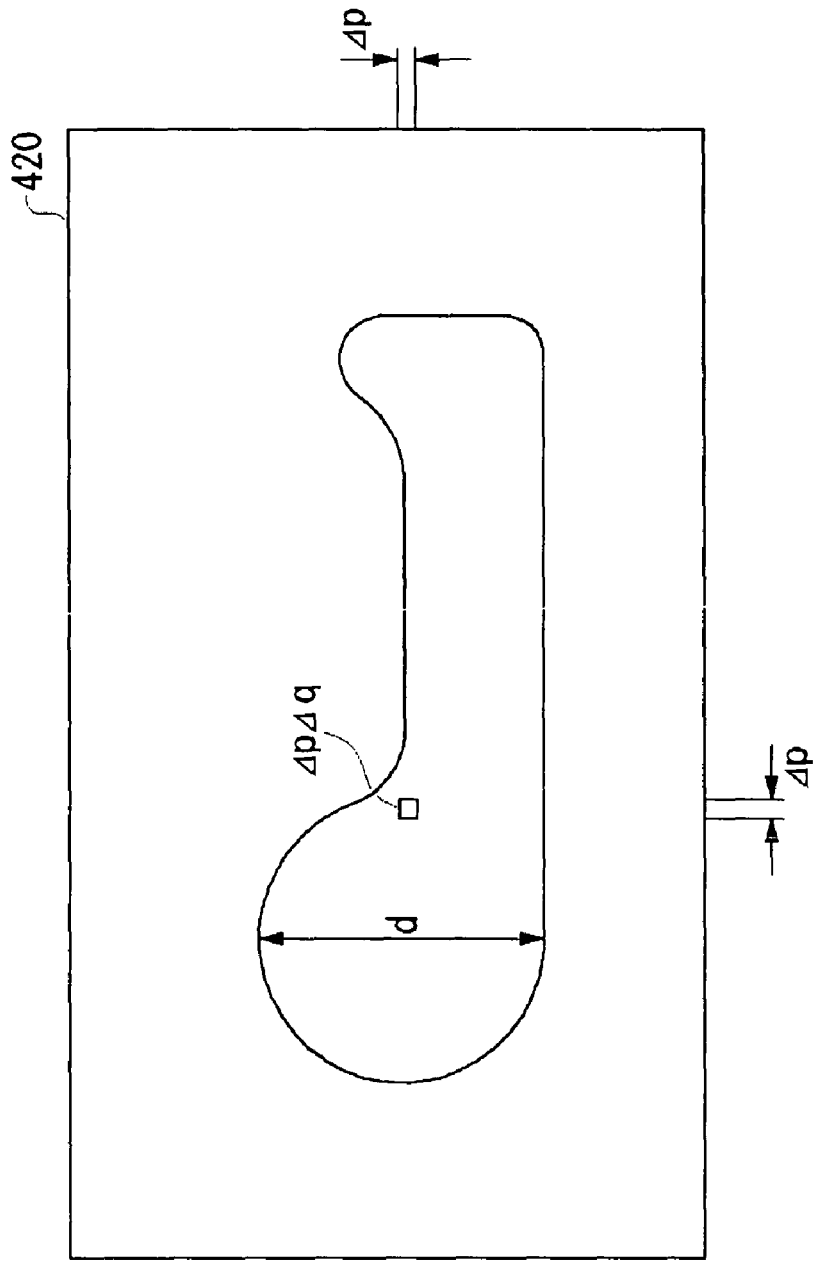
FIG. 15 is a plan view schematically illustrating the thickness of the object 202 which is calculated by a thickness calculating section 152 relating to the different embodiment of the present invention.
Figure 16A:
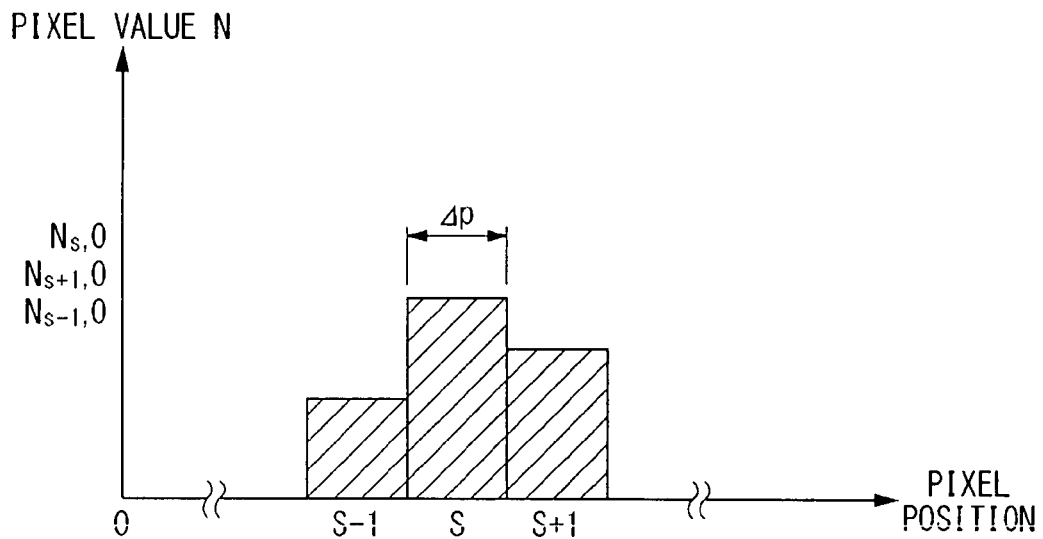
FIGS. 16A and 16B illustrate histograms of the transmission-type images 302a and 302b which are captured by the image-capturing section 100 relating to the different embodiment of the present invention.
Figure 16B:
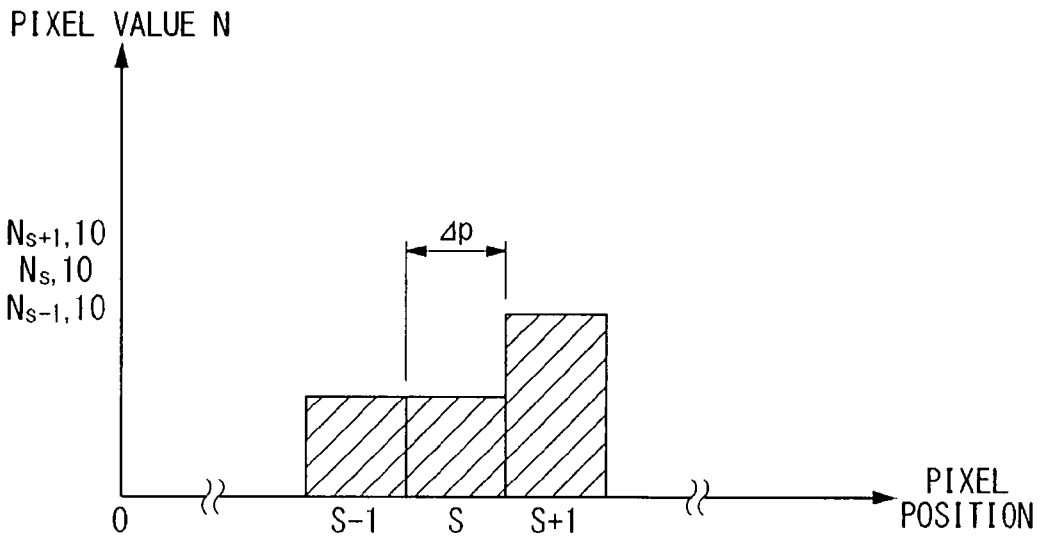
Figure 17A:
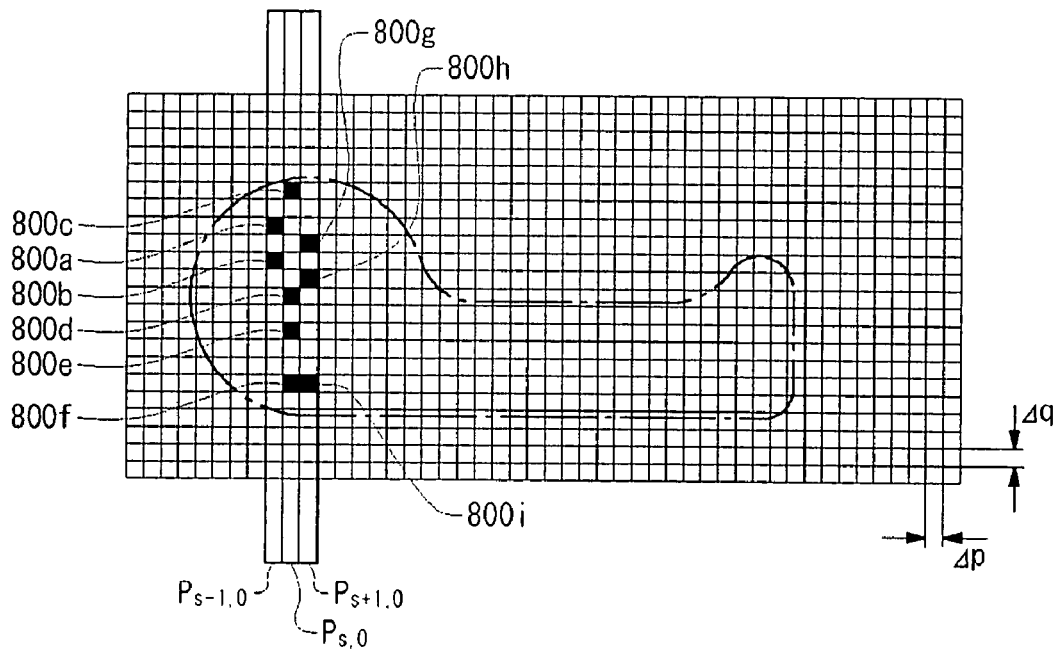
FIGS. 17A and 17B illustrate infinitesimal regions making up a region within the thickness of the object 202, which are defined by a infinitesimal region allocating section 154 relating to the different embodiment of the present invention.
Figure 17B:
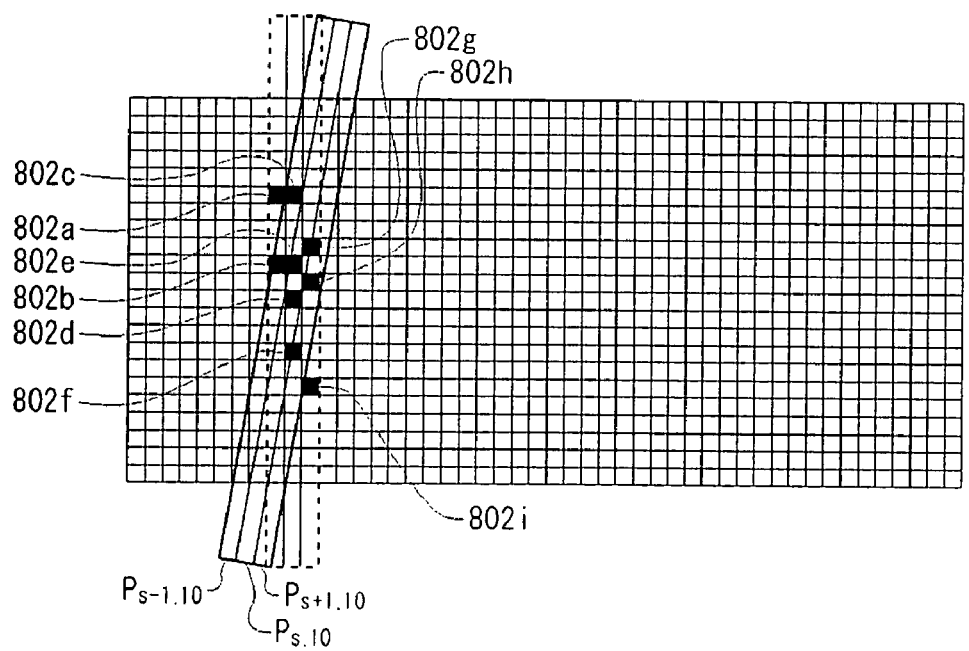

FIG. 15 is a plan view schematically illustrating the thickness of the object 202 which is calculated by the thickness calculating section 152 relating to the different embodiment of the present invention. FIGS. 16A and 16B illustrate histograms of the transmission-type images 302a and 302b which are captured by the image-capturing section 100 relating to the different embodiment of the present invention. FIGS. 17A and 17B each illustrate a infinitesimal region allocated image in which the densities of different levels are allocated by the infinitesimal region allocating section 154 relating to the different embodiment of the present invention.

As shown in FIG. 15, the thickness calculating section 152 calculates the thickness d in the direction in which the electron beam is transmitted through the object 202, based on the spatial distribution of the characteristic regions in the whole object 202 which is calculated by the characteristic region distribution calculating section 140 (step S1052). Note that FIG. 15 shows, as an example of the thicknesses calculated, the thickness d of the object 202 at an auxiliary line A, shown in FIG. 13, which is parallel to the angle of 0° from which the object 202 is image-captured on the plane including the cross-section L. The thickness calculating section 152 divides the thickness d shown in FIG. 15 into infinitesimal regions $\Delta p \Delta q$, in accordance with the infinitesimal regions $\Delta p \Delta q$ included in the infinitesimal region allocated image shown in FIGS. 17A and 17B.

Subsequently, the infinitesimal region allocating section 154 divides the region on the line L in the transmission-type image 302a shown in FIG. 14A into a plurality of infinitesimal regions $\Delta p$ (for example, the pixels having a size of $\Delta p \times \Delta p$) in accordance with the infinitesimal regions $\Delta p \Delta q$ along the thickness shown in FIG. 15 (step S1054). Similarly, the infinitesimal region allocating section 154 divides the region on the line L in the transmission-type image 302b shown in FIG. 14B into a plurality of infinitesimal regions $\Delta p$ in accordance with the infinitesimal regions $\Delta p \Delta q$ along the thickness shown in FIG. 15 (step S1054).

Following this, the infinitesimal region allocating section 154 allocates, to an S-th pixel (pixel S) among the infinitesimal regions $\Delta p$ on the line L in the transmission-type image 302a, a pixel value $N_{S,0}$ which is an integral value determined in proportion to the density as shown in FIG. 16A (step S1056). As an example, the infinitesimal region allocating section 154 judges that the pixel S on the line L in the transmission-type image 302a has a pixel value of $N_{S,0}$ which is selected from the 256 gray levels from black to white. Similarly, the infinitesimal region allocating section 154 allocates, to the pixel S-1 on the line L, a pixel value $N_{S-1,0}$ which is an integral value determined in proportion to the density, for example. Also, the infinitesimal region allocating section 154 allocates, to the pixels corresponding to the infinitesimal regions $\Delta p$ on the line L in the transmission-type image 302b, pixel values which are integral values determined in proportion to the densities as shown in FIG. 16B.

The infinitesimal region allocating section 154 then allocates binary values each indicating a density to the infinitesimal regions included in the infinitesimal region allocated image (step S1058). To perform this allocating operation, the infinitesimal region allocating section 154 first provides a infinitesimal region allocated image in which a two-dimensional screen is divided into infinitesimal regions $\Delta p \Delta q$. After this, referring to a particular angle of 0°, the infinitesimal region allocating section 154 allocates binary values each of which is determined based on the pixel value $N_{S,0}$ allocated to the pixel S as shown in FIG. 16A, to some of the infinitesimal regions ΔpΔq in FIG. 17A (within the region shown by the dashed-dotted line in FIG. 17A) which correspond to the infinitesimal regions along the thickness d shown in FIG. 15. Here, the infinitesimal region allocating section 154 allocates the binary values in such a manner that the total value $K_{S,0}$ of the binary values allocated to the infinitesimal regions ΔpΔq included in the infinitesimal region group $P_{S,0}$ corresponding to the thickness direction along the angle of 0° from which the transmissions-type image 302a is captured becomes equal to the pixel value $N_{S,0}$ of the pixel S on the line L in the transmission-type image 302a.

In the example shown in FIG. 17A, it is assumed that the infinitesimal region allocating section 154 allocates "4" as the pixel value $N_{S,0}$ to the pixel S in the case of the angle of 0°, for example. In this case, the infinitesimal region allocating section 154 allocates white (in FIG. 17A, shown by the black color and the allocated value may be "1") which indicates that the structure is present, to four infinitesimal regions 800c, 800d, 800e, and 800f, among the infinitesimal regions ΔpΔq included in the infinitesimal region group $P_{S,0}$ corresponding to the angle of 0°, so as to satisfy the condition that the total value $K_{S,0}$ of the binary values allocated to the infinitesimal regions ΔpΔq included in the infinitesimal region group $P_{S,0}$ becomes "4". Here, the infinitesimal region allocating section 154 may randomly select the four infinitesimal regions from the infinitesimal regions included in the region corresponding to the thickness d and allocate white to the selected infinitesimal regions.

Subsequently, referring to a different angle of 10°, the infinitesimal region allocating section 154 allocates binary values each indicating a density to the infinitesimal regions included in the infinitesimal region allocated image in such a manner as to still satisfy the condition relating to the angle of 0°. Here, the infinitesimal region allocating section 154 changes the positions of white among the infinitesimal regions which are determined to satisfy the condition relating to the angle of 0°, so that both of the conditions relating to the angles of 0° and 10° are satisfied.

For example, the infinitesimal region allocating section 154 allocates the binary value of "1" to the infinitesimal region 800f as shown in FIG. 17A once, but changes this allocation so as to alternatively allocate the binary value of "1" to a infinitesimal region 802e, in order to maintain, at the same value, the total value $K_{S,0}$ of the binary values allocated to the infinitesimal regions making up the infinitesimal region group $P_{S,0}$ shown in FIG. 17A, and to satisfy the condition that the total value $K_{S,10}$ of the binary values allocated to the infinitesimal regions making up a infinitesimal region group $P_{S,10}$ shown in FIG. 17B becomes equal to the pixel value $N_{S,10}$. FIG. 17B does not show the dashed-dotted line shown in FIG. 17A, but it is also preferable in the infinitesimal region allocated image shown in FIG. 17B that white is allocated to one or more of the infinitesimal regions ΔpΔq which are included in the infinitesimal regions along the thickness d shown in FIG. 15.

The infinitesimal region allocating section 154 allocates white to appropriate ones of the infinitesimal regions included in the infinitesimal region allocated image in such a manner as to satisfy the condition relating to the pixel S on the line L, referring to both of the two angles of 0° and 10°. Furthermore, referring to other angles, the infinitesimal region allocating section 154 also allocates white to appropriate ones of the infinitesimal regions included in the infinitesimal region allocated image in such a manner as to satisfy the condition relating to the pixel S on the line L.

In the above-described manner, the infinitesimal region allocating section 154 allocates binary values each indicating a density to the infinitesimal regions ΔpΔq in the thickness direction which correspond to each of the other pixels on the line L. In addition, the infinitesimal region allocating section 154 allocates the binary values to all of the infinitesimal regions ΔpΔq, within the thickness, on a different cross-section than the cross-section L, i.e. the infinitesimal regions ΔpΔq corresponding to a different line than the line L.

After this, the infinitesimal region allocating section 154 obtains the distribution of the binary values allocated to the infinitesimal regions ΔpΔq in the direction perpendicular to the cross-section L, in other words, in the direction perpendicular to the thickness direction, based on the distribution of the binary values allocated to the infinitesimal regions ΔpΔq within the thickness along each of the lines including the line L. In other words, the infinitesimal region allocating section 154 obtains a density distribution which indicates the distribution of the binary values allocated to the infinitesimal regions ΔpΔq included in the whole object 202. The infinitesimal region allocating section 154 supplies the obtained density distribution to the back projection section 156. The back projection section 156 reconstructs the three-dimensional image of the object 202 by allocating the densities of different levels of the transmission-type images to the obtained density distribution of the object 202.

Specifically speaking, the back projection section 156 develops a normal distribution with respect to the coordinates of white, to generate a weighting function. In accordance with the weighting values calculated by using the generated weighting function, the back projection section 156 back-projects and allocates the densities of different levels of the transmission-type images, to reconstruct the three-dimensional image of the object 202. In this way, the three-dimensional image reconstructing apparatus 20 can highly accurately calculate the respective spatial positions of the characteristic regions and the respective spatial positions of the densities of the infinitesimal regions, thereby being capable of reconstructing a more accurate three-dimensional image of the object 202. Also, the three-dimensional image reconstructing apparatus 20 can reconstruct the three-dimensional image of the object 202 at a high speed, by allocating binary values each indicating a density to the infinitesimal regions within the thicknesses in such a manner as to satisfy the condition relating to the integral values determined in proportion to the densities of different levels of the infinitesimal regions of the transmission-type images. After this, the back projection section 156 outputs the reconstructed three-dimensional image to the output section 180. The output section 180 then outputs the three-dimensional image on which the image processing has been performed by the back projection section 156 to the outside, to provide the user with the three-dimensional image (step S1080).

In the step S1058, the infinitesimal region allocating section 154 allocates binary values to the infinitesimal regions ΔpΔq based on the distribution of the characteristic regions which is calculated in the step S1040 and the thickness calculated in the step S1052. In other words, the three-dimensional image is reconstructed in compliance with the conditions relating to the characteristic regions and thickness, as well as the condition relating to the point distribution based on the densities of different levels. Moreover, the infinitesimal region allocating section 154 may allocate the binary values to the infinitesimal regions ΔpΔq in compliance with the information indicating the known facts which is received in the step S1010. For example, a case is assumed where it is known that the object 202 has a fiber-like internal structure.

When the length, thickness and the like of the fiber-like structure are received, the infinitesimal region allocating section 154 does not allocate white to randomly selected infinitesimal regions. Alternatively, the infinitesimal region allocating section 154 allocates the binary values in such a manner that the group of the infinitesimal regions allocated with white has approximately the same representation as the length and thickness of the fiber-like structure. By doing this, the three-dimensional image reconstructing apparatus 20 relating to the different embodiment of the present invention can more accurately calculate the respective spatial positions of the characteristic regions and the respective spatial regions of the densities of different levels of the infinitesimal regions, based on the information indicating the known facts about the object 202, thereby being capable of reconstructing a more accurate three-dimensional image of the object 202.

The allocation of white to appropriate ones of the infinitesimal regions as illustrated in FIGS. 17A and 17B which is performed with reference to the conditions relating to the transmission-type images is fixed under conditions that the infinitesimal regions allocated with white at the initial setting are distributed in accordance with a predetermined error range by using a method such as multi-stereo measurement, that the maximum distance between adjacent infinitesimal regions allocated with white is limited, and that the actual transmission image matches the projected image or approximated image of the infinitesimal region allocated image. Referring to the last condition, the step S1054 uses a Monte Carlo method as a probabilistic method to reduce the difference between the actual transmission image and the projected image of the infinitesimal region allocated image. Alternatively, a different method such as a genetic algorithm may be used.

Figure 18:
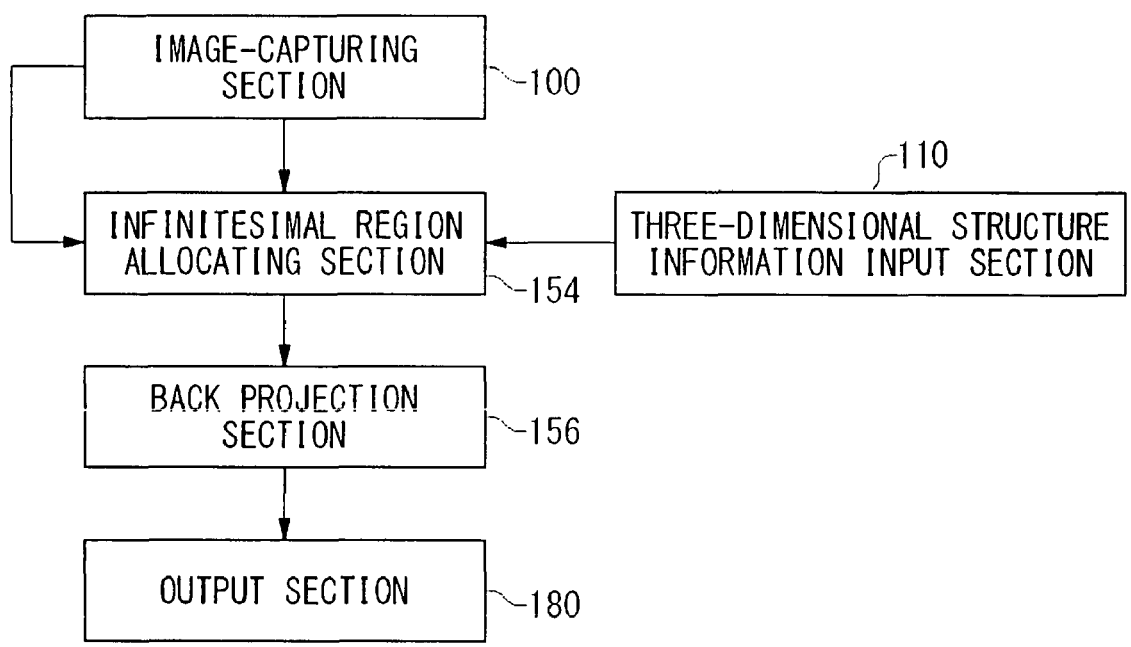
FIG. 18 is a block diagram illustrating an exemplary functional configuration of a three-dimensional image reconstructing apparatus 30 relating to a further different embodiment of the present invention.

FIG. 18 is a block diagram illustrating an exemplary functional configuration of a three-dimensional image reconstructing apparatus 30 relating to a further different embodiment of the present invention. The three-dimensional image reconstructing apparatus 30 is configured so as to be capable of reconstructing the three-dimensional image of the object 202 even when the object 202 has only a small number of characteristic regions and it is difficult to detect the thickness of the object 202. The three-dimensional image reconstructing apparatus 30 includes therein the image-capturing section 100, three-dimensional structure information input section 110, infinitesimal region allocating section 154, back projection section 156, and output section 180. The image-capturing section 100 and three-dimensional structure information input section 110 of the three-dimensional image reconstructing apparatus 30 have the same configurations and functions as the corresponding constituents of the three-dimensional image reconstructing apparatus 20 described with reference to FIGS. 11 to 17, and are therefore not explained herein.

The infinitesimal region allocating section 154 of the three-dimensional image reconstructing apparatus 30 divides the region of an object along a predetermined thickness relating to the object into a plurality of infinitesimal regions, and allocates densities of different levels to the created infinitesimal regions in compliance with the densities of different levels of the transmission-type images captured by the image-capturing section 100. For example, the infinitesimal region allocating section 154 first divides the transmission-type images into a plurality of infinitesimal regions in accordance with the infinitesimal regions included in the region within the predetermined thickness, and allocates integral values determined in proportion to the densities of different levels to the infinitesimal regions of the transmission-type images. The infinitesimal region allocating section 154 then allocates binary values each indicating a density to the infinitesimal regions in the infinitesimal region allocated image within the predetermined thickness in such a manner that the total value of the binary values each indicating a density which are allocated to the infinitesimal regions, along the thickness, which correspond to the angle from which each of the transmission-type images is captured becomes equal to the integral value indicating the density of a corresponding infinitesimal region in each of the transmission-type images. In this way, the infinitesimal region allocating section 154 obtains a density distribution which represents the distribution of the binary values allocated to the infinitesimal regions $\Delta p \Delta q$ in the whole object 202. Here, the infinitesimal region allocating section 154 obtains the information indicating the known facts about the three-dimensional structure of the object from the three-dimensional structure information input section 110, and allocates the densities of different levels to the infinitesimal regions in compliance with the received information indicating the known facts. The infinitesimal region allocating section 154 supplies the obtained density distribution to the back projection section 156. The back projection section 156 reconstructs the three-dimensional image of the object 202 by allocating the densities of different levels of the transmission-type images to the obtained density distribution of the object 202. The back projection section 156 outputs the reconstructed three-dimensional image to the output section 180. Here, the predetermined thickness is, for example, the whole infinitesimal region allocated image which has a rectangular shape and a predetermined size. Another example of the predetermined thickness is the thickness or shape of the object, when the approximate thickness or shape is known.

Figure 19:
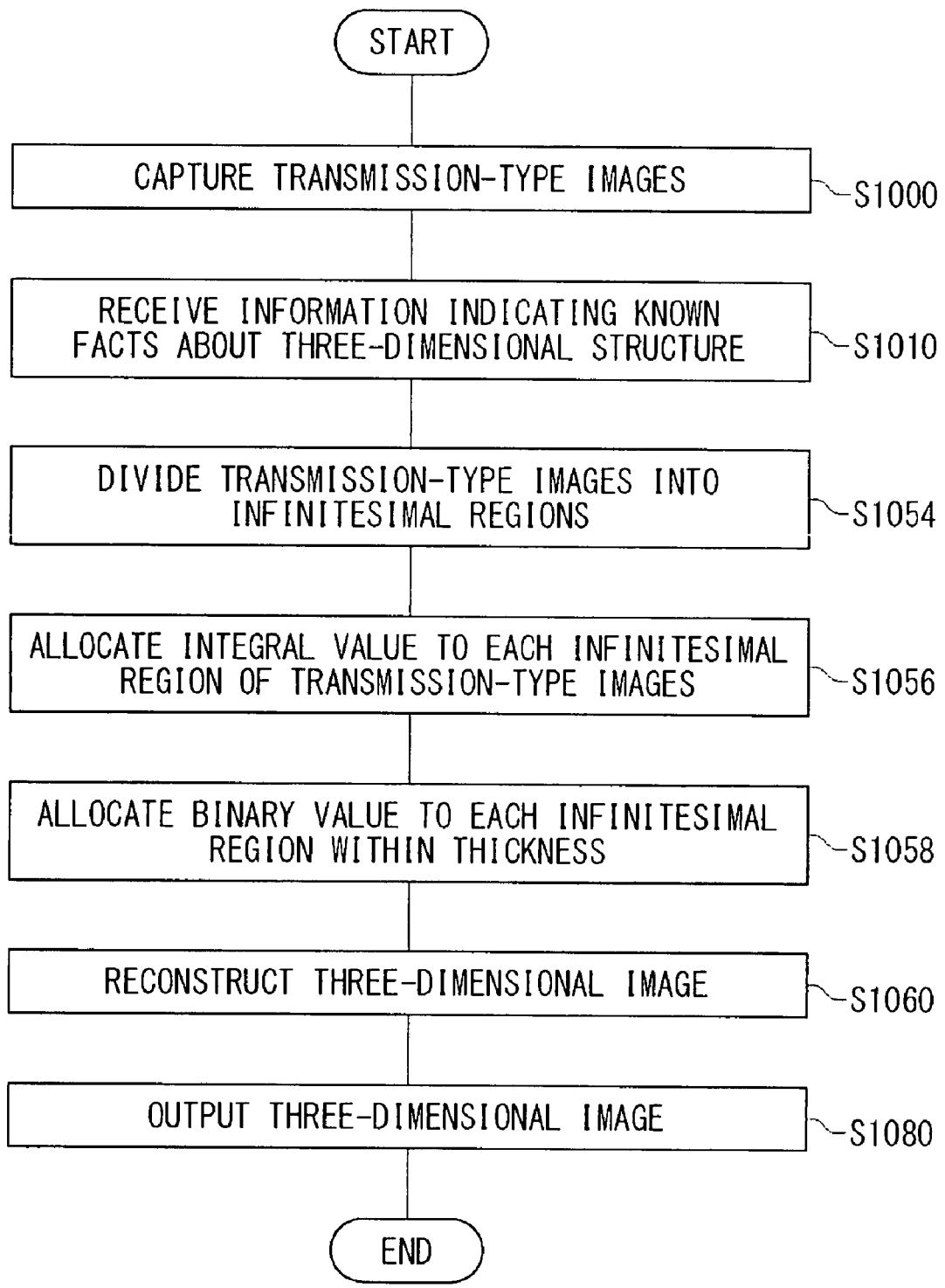
FIG. 19 is a flow chart illustrating an exemplary flow of processes making up a three-dimensional image reconstructing method which is conducted by using the three-dimensional image reconstructing apparatus 30 relating to the further different embodiment of the present invention.

FIG. 19 is a flow chart illustrating an exemplary flow of processes making up a three-dimensional image reconstructing method which is conducted by using the three-dimensional image reconstructing apparatus 30 relating to the further different embodiment of the present invention. The three-dimensional image reconstructing methods preformed by using the three-dimensional image reconstructing apparatuses 20 and 30 share the same processes. In the following description of the flow chart shown in FIG. 19, such shared processes are not fully explained.

As shown in FIG. 13, the image-capturing section 100 captures the transmission-type images 302a and 302b each including therein the object 202 which are shown in FIGS. 14A and 14B, by transmitting an electron beam through the object 202 from an angle of 0° and a different angle of 10° on one plane including the cross-section L of the object 202 (step S1000).

Subsequently, the three-dimensional structure information input section 110 receives the information indicating the known facts about the object 202 (step S1010). After this, the infinitesimal region allocating section 154 divides the region along the line L in the transmission-type images 302a and 302b into the infinitesimal regions $\Delta p$ in accordance with the infinitesimal regions $\Delta p \Delta q$ included in the region along the thickness shown in FIG. 15 (step S1054). The infinitesimal region allocating section 154 then allocates the integral values determined in proportion to the densities of different levels, to the infinitesimal regions $\Delta p$ along the line L in the transmission-type images 302a and 302b, as pixel values (step S1056). The infinitesimal region allocating section 154 subsequently allocates the binary values to the infinitesimal regions $\Delta p \Delta q$ within the thickness of the infinitesimal region allocated image, for example, the infinitesimal regions $\Delta p \Delta q$ included in the whole rectangular-shaped infinitesimal region allocated image (step S1058). In this way, the three-dimensional image reconstructing apparatus 30 allocates the binary values each indicating a density to the infinitesimal regions within the thickness in such a manner as to satisfy the condition relating to the integral values determined in proportion to the densities of different levels of the infinitesimal regions of the transmission-type images, thereby being capable of reconstructing the three-dimensional image of the object 202 at a high speed.

Here, the infinitesimal region allocating section 154 allocates the binary values to the infinitesimal regions $\Delta p \Delta q$ in compliance with the information about the known facts received in the step S1010. In this way, the three-dimensional image reconstructing apparatus 30 can calculate, with a higher accuracy, the respective spatial positions of the densities of the infinitesimal regions based on the information indicating the known facts about the object 202, thereby being capable of reconstructing a more accurate three-dimensional image of the object 202.

Subsequently, the infinitesimal region allocating section 154 obtains the density distribution based on the distribution of the binary values allocated to all the infinitesimal regions $\Delta p \Delta q$ within the thicknesses along the lines including the line L. The infinitesimal region allocating section 154 supplies the obtained density distribution to the back projection section 156. The back projection section 156 reconstructs the three-dimensional image of the object 202 by allocating the densities of different levels of the transmission-type images onto the obtained density distribution of the object 202 (step S1060). The back projection section 156 outputs the reconstructed three-dimensional image to the output section 180. The output section 180 outputs the three-dimensional image which has been subjected to the image processing by the infinitesimal region allocating section 154 to the outside, so as to provide the user with the three-dimensional image (step S1080).

The above-described three-dimensional image reconstructing apparatuses 20 and 30 reconstruct the three-dimensional image in compliance with the condition relating to the point distribution of the transmission-type images. Therefore, the three-dimensional image reconstructing apparatuses 20 and 30 can reconstruct a more accurate three-dimensional image based on the same number of transmission-type images as in a case where a different method such as CT scan is used, and reconstruct a three-dimensional image having substantially the same accuracy as in the case where the different method is used, based on transmission-type images the number of which is approximately one-tenth when compared to the case where the different method is used. As a result, the three-dimensional image reconstructing apparatuses 20 and 30 can reconstruct a three-dimensional image based on an insufficient set of transmission-type images, when transmission-type images from all the directions can not be obtained, for example. Also, the three-dimensional image reconstructing apparatuses 20 and 30 can complement the insufficient set of transmission-type images by defining conditions relating to the information about the known facts, for example, "an isolated point is not permitted", "the dispersion falls within a predetermined range" or the like, in addition to the above-mentioned condition relating to the point distribution, so as to reconstruct a three-dimensional image or a more accurate three-dimensional image.

Referring to the three-dimensional image reconstructing methods performed by using the three-dimensional image reconstructing apparatuses 20 and 30, the number of transmission-type images to be captured and the particle size of the infinitesimal region $\Delta p \Delta q$ in the region within the thickness of the object 202 may preferably be set in accordance with information indicating whether the structure of the object 202 is known or not, or, if the structure is known, in accordance with information indicating the known approximate structure. For example, the image-capturing section 100 may capture the transmission-type images by varying the image-capturing angle in units of an angle larger or smaller than 10° in accordance with the above-mentioned information, in the present embodiment.

While one aspect of the present invention has been described through the embodiments, the technical scope of the invention is not limited to the above described embodiments. It is apparent to persons skilled in the art that various alternations and improvements can be added to the above-described embodiments. It is also apparent from the scope of the claims that the embodiments added with such alternations or improvements can be included in the technical scope of the invention.

What is claimed is:

1. A three-dimensional image reconstructing apparatus for reconstructing a three-dimensional image showing a three-dimensional structure of an object based on an image of the object which is obtained by image-capturing the object, comprising:
   a processor;
   an image-capturing section that captures a plurality of transmission-type images by transmitting an electron beam through the object from a plurality of different angles, the captured transmission-type images each being represented by densities of different levels and including the object;
   a characteristic region selecting section that selects a plurality of characteristic regions included in the object in each of the transmission-type images;
   a characteristic region distribution calculating section that calculates respective spatial positions of the characteristic regions in the whole object based on respective positions of the characteristic regions, in the each of the transmission-type images, which are selected in the each of the transmission-type images, so as to calculate a spatial distribution of the characteristic regions in the whole object; and
   a three-dimensional image reconstructing section that, when reconstructing the three-dimensional image which shows the three-dimensional structure of the object and in which the densities of different levels are allocated to the whole object by integrating the transmission-type images, allocates the densities of different levels of the transmission-type images to respective positions, in the three-dimensional image, of the characteristic regions based on the spatial distribution of the characteristic regions in the whole object, so as to reconstruct the three-dimensional image in which a three-dimensional structure in each of the characteristic regions is shown.

2. The three-dimensional image reconstructing apparatus as set forth in claim 1, further comprising:
   a three-dimensional structure information input section that receives information indicating an approximate three-dimensional structure of the object; and
   an enhancement processing section that performs image processing to enhance the object in each of the transmission-type images based on the received information indicating the approximate three-dimensional structure, wherein
   the characteristic region selecting section selects the characteristic regions included in the object which is enhanced by the enhancement processing section, in each of the transmission-type images.

3. The three-dimensional image reconstructing apparatus as set forth in claim 1, wherein
the characteristic region distribution calculating section calculates the respective spatial positions of the characteristic regions in the whole object, based on a position, in the each of the transmission-type images, of an outline of the object which is included in each of the characteristic regions.

4. The three-dimensional image reconstructing apparatus as set forth in claim 2, wherein
the image-capturing section captures the transmission-type images each including the object an inside of which is stained, or the inside of which is not stained but which has a three-dimensional structure based on a density distribution.

5. The three-dimensional image reconstructing apparatus as set forth in claim 3, wherein
the image-capturing section captures the transmission-type images each including the object an inside of which is stained, or the inside of which is not stained but which has a three-dimensional structure based on a density distribution.

6. The three-dimensional image reconstructing apparatus as set forth in claim 1, further comprising:
a matching operation calculating section that calculates an image processing operation to determine the densities of a three-dimensional image, which is reconstructed by the three-dimensional image reconstructing section, of any of the characteristic regions which has a known three-dimensional structure, so that the densities of the three-dimensional image of the characteristic region which has the known three-dimensional structure match the known three-dimensional structure; and
a matching operation section that performs the image processing operation calculated by the matching operation calculating section on densities of a three-dimensional image, which is reconstructed by the three-dimensional image reconstructing section, of any of the characteristic regions which has an unknown three-dimensional structure.

7. The three-dimensional image reconstructing apparatus as set forth in claim 1, wherein
the three-dimensional image reconstructing section includes:
a thickness calculating section that calculates a thickness of the object in a direction in which the electron beam is transmitted through the object, based on the spatial distribution of the characteristic regions which is calculated by the characteristic region distribution calculating section; and
a infinitesimal region allocating section that divides, into a plurality of infinitesimal regions, a region within the thickness of the object which is calculated by the thickness calculating section, and allocates densities of different levels to the infinitesimal regions in compliance with the densities of different levels of the transmission-type images captured by the image-capturing section.

8. The three-dimensional image reconstructing apparatus as set forth in claim 7, wherein
the infinitesimal region allocating section (i) divides each of the transmission-type images into a plurality of infinitesimal regions in correspondence with the infinitesimal regions making up the region within the thickness of the object, (ii) allocates integral values determined in proportion to the densities of different levels respectively to the infinitesimal regions included in the each of the transmission-type images, and (iii) allocates binary values each indicating a density to the infinitesimal regions making up the region within the thickness in such a manner that a total value of binary values each indicating a density which are allocated to some of the infinitesimal regions making up the region within the thickness which correspond to an angle from which the each of the transmission-type images is captured becomes equal to an integral value indicating a density which is allocated to a corresponding one of the infinitesimal regions included in the each of the transmission-type images.

9. The three-dimensional image reconstructing apparatus as set forth in claim 7, further comprising
a three-dimensional structure information input section that receives information indicating known facts about the three-dimensional structure of the object, wherein
the infinitesimal region allocating section allocates the densities of different levels to the infinitesimal regions in compliance with the information indicating the known facts which is received by the three-dimensional structure information input section.

10. A three-dimensional image reconstructing apparatus for reconstructing a three-dimensional image showing a three-dimensional structure of an object based on an image of the object which is obtained by image-capturing the object, comprising:
a processor;
an image-capturing section that captures a plurality of transmission-type images by transmitting an electron beam through the object from a plurality of different angles, the transmission-type images each being represented by densities of different levels and including the object; and
a infinitesimal region allocating section that divides, into a plurality of infinitesimal regions, a region within a predetermined thickness relating to the object, and reconstructs the three-dimensional image of the object by allocating a density of a certain level to each of the infinitesimal regions in compliance with the densities of different levels of the transmission-type images captured by the image-capturing section.

11. The three-dimensional image reconstructing apparatus as set forth in claim 10, wherein
the infinitesimal region allocating section (i) divides each of the transmission-type images into a plurality of infinitesimal regions in correspondence with the infinitesimal regions making up the region within the thickness of the object, (ii) allocates integral values determined in proportion to the densities of different levels respectively to the infinitesimal regions included in the each of the transmission-type images, and (iii) allocates binary values each indicating a density to the infinitesimal regions making up the region within the thickness in such a manner that a total value of binary values each indicating a density which are allocated to some of the infinitesimal regions making up the region within the thickness which correspond to an angle from which the each of the transmission-type images is captured becomes equal to an integral value indicating a density which is allocated to a corresponding one of the infinitesimal regions included in the each of the transmission-type images.

12. The three-dimensional image reconstructing apparatus as set forth in claim 10, further comprising
a three-dimensional structure information input section that receives information indicating known facts about the three-dimensional structure of the object, wherein the infinitesimal region allocating section allocates the densities of different levels to the infinitesimal regions in compliance with the information indicating the known facts which is received by the three-dimensional structure information input section.

13. A three-dimensional image reconstructing method for reconstructing a three-dimensional image showing a three-dimensional structure of an object based on an image of the object which is obtained by image-capturing the object, comprising using a computer to perform the steps of:
   capturing a plurality of transmission-type images by transmitting an electron beam through the object from a plurality of different angles, the captured transmission-type images each being represented by densities of different levels and including the object;
   selecting a plurality of characteristic regions included in the object in each of the transmission-type images;
   calculating respective spatial positions of the characteristic regions in the whole object based on respective positions of the characteristic regions, in the each of the transmission-type images, which are selected in the each of the transmission-type images, so as to calculate a spatial distribution of the characteristic regions in the whole object; and
   allocating the densities of different levels of the transmission-type images to respective positions, in the three-dimensional image, of the characteristic regions based on the spatial distribution of the characteristic regions in the whole object, so as to reconstruct the three-dimensional image in which a three-dimensional structure in each of the characteristic regions is shown, when the three-dimensional image which shows the three-dimensional structure of the object and in which the densities of different levels are allocated to the whole object is reconstructed by integrating the transmission-type images.

14. A three-dimensional image reconstructing method for reconstructing a three-dimensional image showing a three-dimensional structure of an object based on an image of the object which is obtained by image-capturing the object, comprising using a computer to perform the steps of:
   capturing a plurality of transmission-type images by transmitting an electron beam through the object from a plurality of different angles, the transmission-type images each being represented by densities of different levels and including the object; and
   dividing, into a plurality of infinitesimal regions, a region within a predetermined thickness relating to the object, and reconstructing the three-dimensional image of the object by allocating a density of a certain level to each of the infinitesimal regions in compliance with the densities of different levels of the transmission-type images captured in the image-capturing.

15. A non-transitory computer readable medium storing thereon a three-dimensional image reconstructing program which causes a computer to function as a three-dimensional image reconstructing apparatus for reconstructing a three-dimensional image showing a three-dimensional structure of an object based on an image of the object which is obtained by image-capturing the object, the program causing the computer to function as:
   an image-capturing section that captures a plurality of transmission-type images by transmitting an electron beam through the object from a plurality of different angles, the captured transmission-type images each being represented by densities of different levels and including the object;
   a characteristic region selecting section that selects a plurality of characteristic regions included in the object in each of the transmission-type images;
   a characteristic region distribution calculating section that calculates respective spatial positions of the characteristic regions in the whole object based on respective positions of the characteristic regions, in the each of the transmission-type images, which are selected in the each of the transmission-type images, so as to calculate a spatial distribution of the characteristic regions in the whole object; and
   a three-dimensional image reconstructing section that, when reconstructing the three-dimensional image which shows the three-dimensional structure of the object and in which the densities of different levels are allocated to the whole object by integrating the transmission-type images, allocates the densities of different levels of the transmission-type images to respective positions, in the three-dimensional image, of the characteristic regions based on the spatial distribution of the characteristic regions in the whole object, so as to reconstruct the three-dimensional image in which a three-dimensional structure in each of the characteristic regions is shown.

16. A non-transitory computer readable medium storing thereon a three-dimensional image reconstructing program which causes a computer to function as a three-dimensional image reconstructing apparatus for reconstructing a three-dimensional image showing a three-dimensional structure of an object based on an image of the object which is obtained by image-capturing the object, the program causing the computer to function as:
   an image-capturing section that captures a plurality of transmission-type images by transmitting an electron beam through the object from a plurality of different angles, the transmission-type images each being represented by densities of different levels and including the object; and
   a infinitesimal region allocating section that divides, into a plurality of infinitesimal regions, a region within a predetermined thickness relating to the object, and reconstructs the three-dimensional image of the object by allocating a density of a certain level to each of the infinitesimal regions in compliance with the densities of different levels of the transmission-type images captured by the image-capturing section.

* * * * *